United States Patent [19]

Kimura et al.

[11] Patent Number: 5,335,662
[45] Date of Patent: Aug. 9, 1994

[54] IMAGE PICKUP SYSTEM COMPRISING SIGNAL PROCESSING DEVICE WHICH USES EXCLUSIVE ADAPTOR IN PROBES DIFFERENT IN IMAGE PICKUP SYSTEM FROM EACH OTHER

[75] Inventors: Kenji Kimura, Tachikawa; Kiyoshi Tsuji, Musashino, both of Japan

[73] Assignee: Olympus Optical Co., Ltd., Tokyo, Japan

[21] Appl. No.: 81,141

[22] Filed: Jun. 25, 1993

[30] Foreign Application Priority Data

Aug. 28, 1992 [JP] Japan .................................. 4-230337

[51] Int. Cl.5 .............................................. A61B 8/00
[52] U.S. Cl. ......................... 128/662.03; 128/660.01; 73/628
[58] Field of Search ............ 73/621, 628; 128/24 AA, 128/662.06, 660.01, 662.03; 367/7

[56] References Cited

U.S. PATENT DOCUMENTS

| 4,244,227 | 1/1981 | Rudolph et al. ................... 73/621 |
| 4,811,740 | 3/1989 | Ikeda et al. ................... 128/660.01 |
| 4,909,240 | 3/1990 | Helmreich et al. ............ 128/24 AA |
| 5,140,558 | 8/1992 | Harrison, Jr. et al. ................. 367/7 |
| 5,205,175 | 4/1993 | Garza et al. ........................... 73/628 |
| 5,209,235 | 5/1993 | Brisken et al. .................. 128/662.06 |

Primary Examiner—Angela D. Sykes
Assistant Examiner—George Manuel
Attorney, Agent, or Firm—Armstrong, Westerman, Hattori, McLeland and Naughton

[57] ABSTRACT

A plurality of probes having image pickup elements differing from each other in image pickup system from each other are used to display an image image-picked-up on a monitor, and a connector of the used image pickup probe is connected to an exclusive adaptor, whereby a drive adapted for the image pickup element is applied to subject the image pickup element to preprocess processing suited for an output signal outputted from the image pickup element. The adaptor is mounted on a signal processing apparatus body, whereby substantially common process processing is subjected to a signal after the preprocess processing by the signal processing apparatus body, to generate a standard image signal. Thus, the standard image signal is displayed on a monitor.

71 Claims, 26 Drawing Sheets

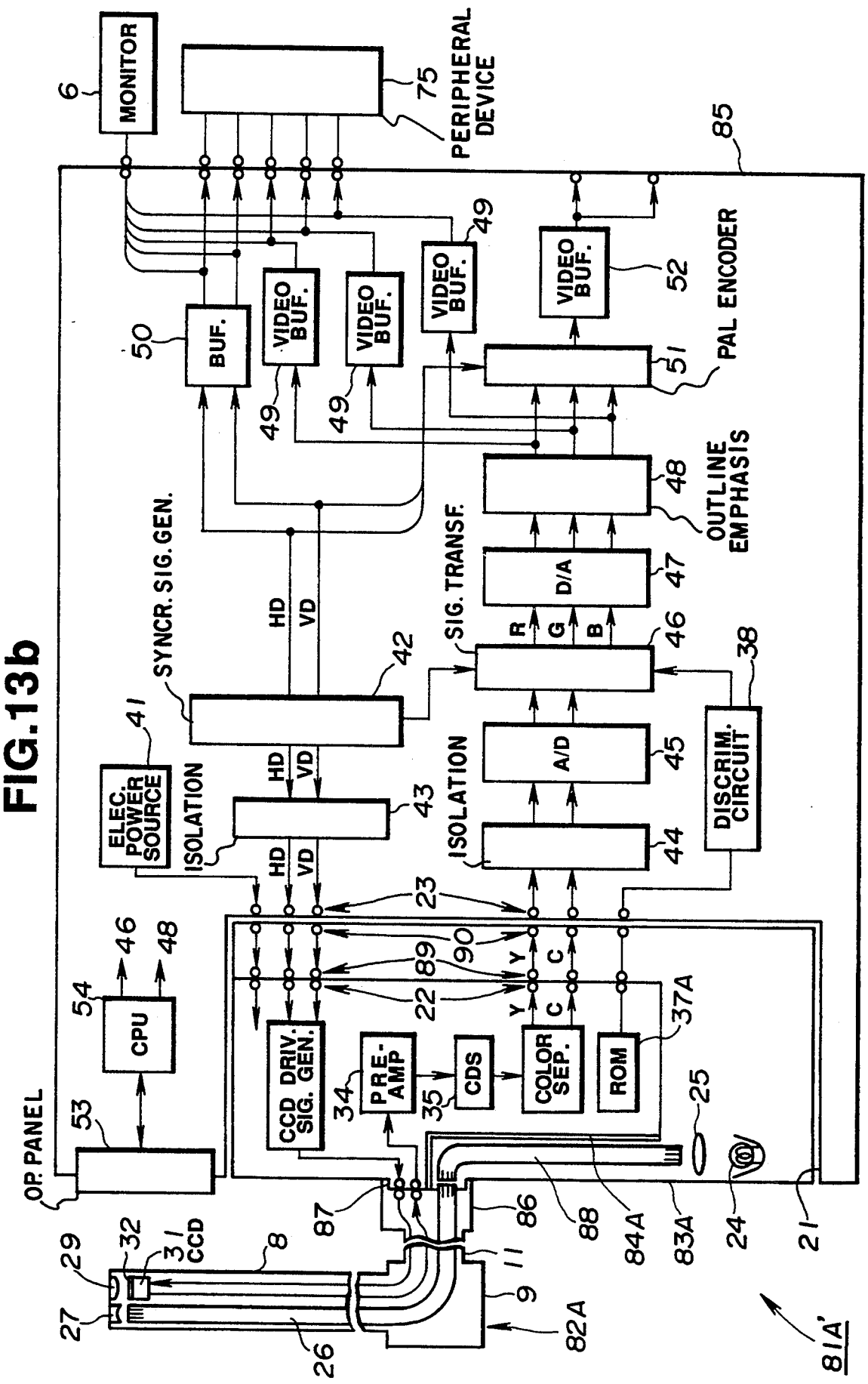

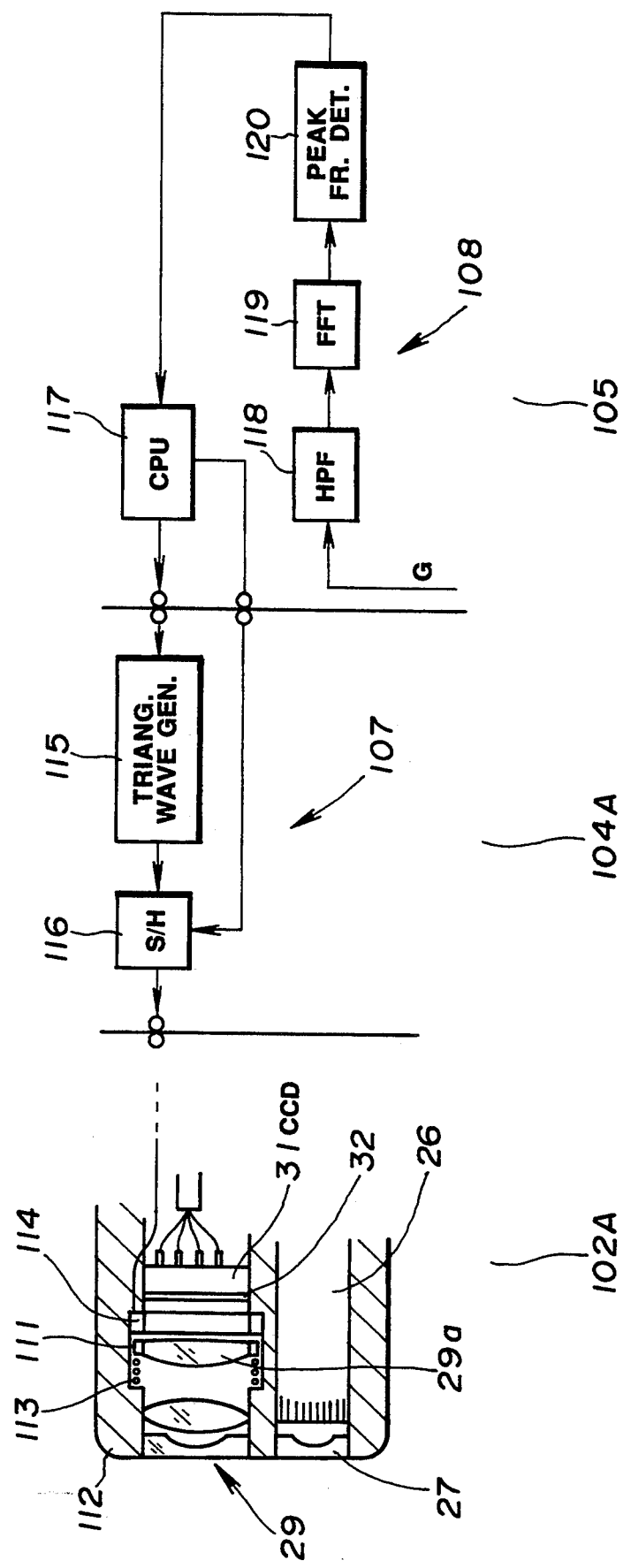

IMAGE PICKUP SYSTEM COMPRISING SIGNAL PROCESSING DEVICE WHICH USES EXCLUSIVE ADAPTOR IN PROBES DIFFERENT IN IMAGE PICKUP SYSTEM FROM EACH OTHER

BACKGROUND OF THE INVENTION

1. Field of the Invention

The present invention relates to an image pickup system comprising a signal processing device in which an exclusive adaptor is mounted on a body of the signal processing device in accordance with probes such as those used in electronic scopes or the like, whereby the signal processing device is capable of processing a signal with respect to probes which have different image pickup systems.

2. Description of the Related Art

In recent years, an endoscope has widely been used in which elongated inserting section is inserted into a body, Whereby an affected or diseased part or the like illuminated from a forward end of the inserting section is observable by light which is taken or fetched thereinto through an objective lens provided on an observation window.

Further, an electronic endoscope system has also been put to practical use wherein an electronic endoscope is used in which an image pickup element such as a CCD or the like is arranged on a focal surface or plane of an objective lens, and a signal photoelectrically transferred by the image pickup element is processed by a signal processing device, whereby an image of a subject can be displayed on a monitor.

In a case of the electronic endoscope, if the numbers of picture elements of the image pickup devices differ from each other, it is necessary to also replace or change the signal processing of the signal processing device. As a prior art example, Japanese Patent Laid-Open No. SHO 63-260527 (260527/1988) discloses an electronic endoscope system in which a signal processing device section is unitized in correspondence to the number of picture elements of the electronic endoscope, and an exclusive unit is mounted on and is used in accordance with electronic endoscopes different in the number of picture elements from each other, whereby the electronic endoscope system can cope with electronic endoscopes differing from each other in the number of picture elements.

However, in the image pickup system of the electronic endoscope, there exist a concurrent type in which a color image is produced under white light illumination, and also a surface sequential type in which image pickup is performed under surface sequential illuminating light which performs sequential illumination by illuminating lights differing from each other in wavelength regions to produce a color image. The above-described prior art can deal with a case where just the number of picture elements differ from each other, but cannot deal with a case where the image pickup systems themselves are different from each other.

In a case where the image pickup systems are different from each other, replacement of the entire signal processing device is expensive. Accordingly, a system is desired which can deal also with a case where the image pickup systems are different from each other, at low cost.

Therefore, it is desirable to utilize a system which can selectively use electronic endoscopes having image pickup systems which differ from each other in regard to the status or circumstances of performance of inspection/diagnosis. Accordingly, more efficient endoscope inspection/diagnosis is made possible.

For example, when the type of endoscope is used in which the color image is produced under the white illumination, color shear generation is minimized even in a case where a subject large in motion is image-picked-up. Accordingly, the concurrent type is effective in a case where an internal organ in the vicinity of a heart is inspected/diagnosed.

On the other hand, in a case .Where an internal organ remote from the heart or within a narrow lacuna in which motion or movement is minimal is inspected/diagnosed, if the surface sequential type is utilized, there is produced an endoscope image which has resolution of the order of three (3) times greater than the case of the concurrent type (it is assumed that the image pickup elements the same in size as each other are used both in the concurrent type and in the surface sequential type). Accordingly, an abnormal portion can be discriminated in detail.

On the other hand, in a case where an internal organ adjacent to the heart is inspected/diagnosed, if only the electronic endoscope of surface sequential type is used, there is a possibility that an image is brought to an endoscope image in which there is a significant amount of color shear. In this case, even if the electronic endoscope different in the number of picture elements from the previous endoscope is used, as in the prior art, an improvement cannot be expected.

Moreover, in a case where a part within the narrow lacuna is inspected/diagnosed, if only the electronic endoscope which provides a color image under white light illumination is used, it becomes difficult to produce an image high in resolution. In this case, if the electronic endoscope large or high in the number of picture elements is used, the resolution is improved. However, since the size of an image pickup element also increases, it becomes difficult to insert the electronic endoscope into the narrow lacuna.

Accordingly, in order to produce more effective endoscope inspection/diagnose results, it is desirable to realize, at low cost, a system also selectively used among various electronic endoscopes which differ from each other in their image pickup systems, as described previously.

Furthermore, the above-described prior art cannot cope with a case of a system which can selectively use the electronic endoscope and an ultrasonic scope capable of producing an ultrasonic image which is different in kind or type from an image in which an optical image due to the electronic endoscope is photoelectrically transferred.

If the system is an image pickup system which can be used also in the ultrasonic scope in which acoustic image information different from optical image information due to the electronic endoscope can be reduced with respect to an inspection object such as an affected or diseased part or the like, more effective information in a case of inspection/diagnoses can be produced.

Further, if the system can change a system arrangement at low cost from the electronic endoscope system as occasion demands, to a system arrangement suitable for inspection/diagnoses, the system becomes extremely effective in performing inspection/diagnoses.

SUMMARY OF THE INVENTION

It is an object of the invention to provide an image pickup system which can cope with a probe provided with image pickup elements differing from each other in the image pickup system, with a necessary minimum change and which can reduce cost.

It is another object of the invention to provide an image pickup system which can change a system arrangement at low cost, and which can facilitate the changing operation.

According to the invention, there is provided an image pickup system comprising:

- a first probe having an elongated first inserting section, and first image pickup means arranged adjacent to a forward end of the first inserting section, for taking an image of an object;
- a second probe having an elongated second inserting section, and second image pickup means arranged adjacent to a forward end of the second inserting section and different in signal form/function from the first image pickup means;
- a first adaptor unit connected to the first probe through a cable for generating a drive signal adapted for signal form/function of the first image pickup means;
- a second adaptor unit connected to the second probe through a cable for generating a drive signal adapted for signal form/function of the second image pickup means, the second adaptor unit being separate from the first adaptor unit;
- a body unit having a connecting portion to which the first and second adaptor units are detachably connected, the body unit performing signal processing adapted for the first and second image pickup means, to generate a standard image signal; and
- monitor connected to the body unit, for displaying the image signal.

According to the invention, there is further provided a signal processing unit comprising:

- first and second adaptor units to which first and second probes having respectively first and second image pickup means differing from each other in signal form/function are connectable, for generating drive signals adapted respectively to the first and second image pickup means, the first and second adaptor units having first and second adaptor units separate from each other; and
- a body unit having a connecting portion to which the first and second adaptor units are detachably connected, the body unit performing signal processing adapted to the first and second image pickup means and generates a common image signal.

BRIEF DESCRIPTION OF THE DRAWINGS

FIG. 2 is a block diagram showing an arrangement of an electronic endoscope system of concurrent type;

FIG. 3 is a block diagram showing an arrangement of an electronic endoscope system of surface sequential type;

FIG. 4 is a block diagram showing an arrangement of a signal conversion circuit;

FIG. 5 is an arrangement view of a light source unit of surface sequential type;

FIG. 6 is a view for explanation showing an output signal of a drive-signal generating circuit;

FIG. 9 is a block diagram showing a principal portion of an arrangement of an electronic endoscope system of surface sequential type;

FIG. 12 is a block diagram showing an arrangement of an electronic endoscope system of surface sequential type;

FIG. 13b is a block diagram showing an of an electronic endoscope system of concurrent type according to a second modification of the third embodiment of the invention;

FIGS. 14 and 15 relate to a fourth embodiment of the invention, FIG. 14 being an arrangement view of an electronic endoscope system of concurrent type according to the fourth embodiment of the invention;

FIG. 15 is a view for explanation showing an autofocus mechanism;

FIG. 17 is an arrangement view showing principal portions of electronic endoscope systems for infrared and for visibility;

FIG. 22 is a view for explanation showing the fact that display sizes of an endoscope image on a monitor are different from each other;

DETAILED DESCRIPTION OF THE PREFERRED EMBODIMENTS

Various embodiments of the invention will hereunder be described with reference to the accompanying drawings.

Figure 1:
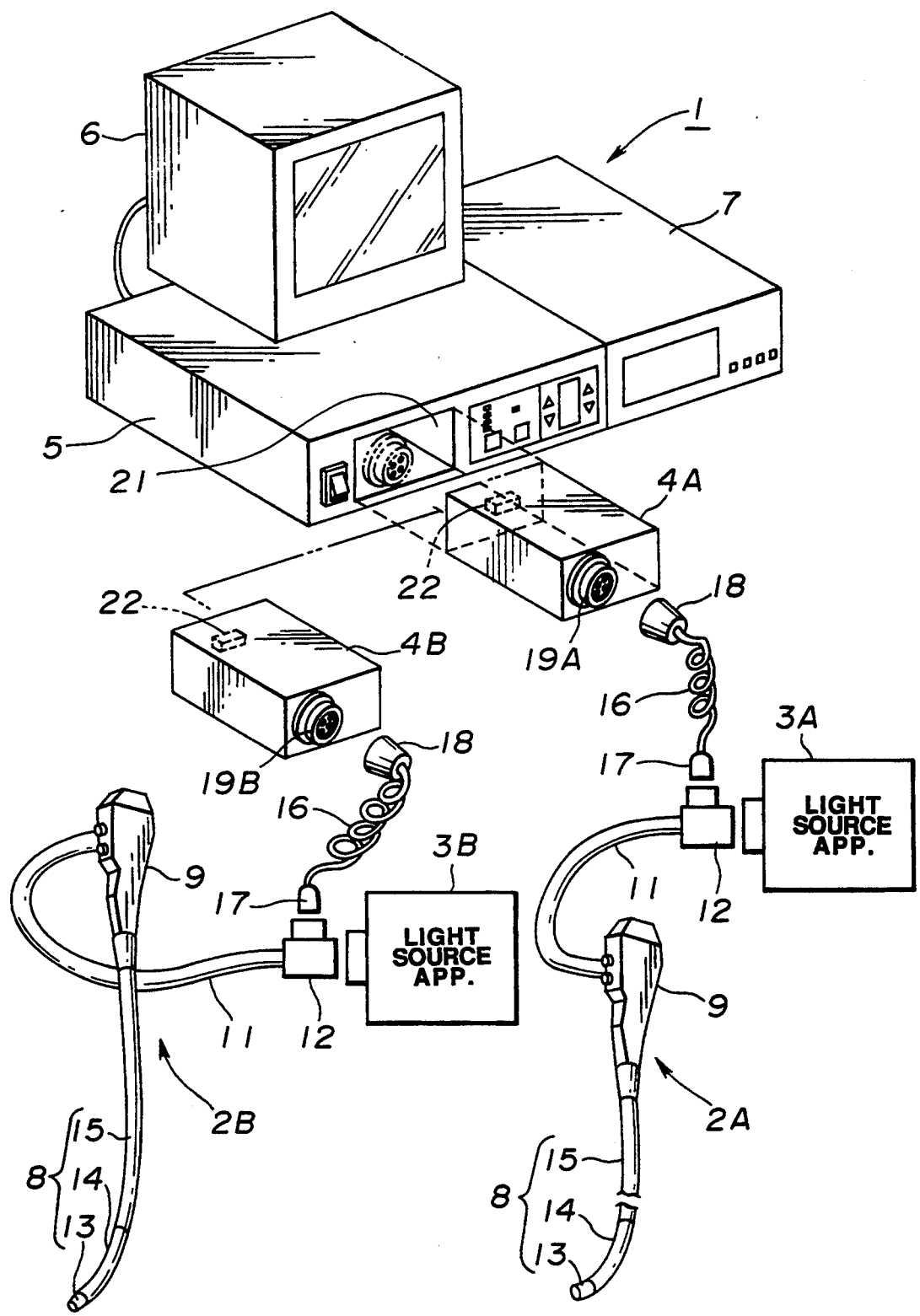
FIGS. 1 to 6 relate to a first embodiment of the invention, FIG. 1 being an entire arrangements view showing an electronic endoscope system according to a first embodiment of the invention.

As shown in FIG. 1, an electronic endoscope system 1 according to a first embodiment of the invention comprises a pair of electronic endoscopes (hereinafter referred also to "electronic scopes") 2A and 2B differing from each other in their image pickup systems, a pair of light source units 3A and 3B for supplying illuminating light adapted respectively for the electronic scopes 2A and 2B, a pair of adaptors 4A and 4B for outputting drive signals adapted respectively for the electronic scopes 2A and 2B, a signal processing unit body (referred also to "video processor body") 5 on which the adaptors 4A and 4B exclusive for the electronic scopes 2A and 2B are detachably mounted, for performing substantially common signal processing, a color monitor 6 for displaying a standard image signal outputted from a signal output end of the video processor body 5, and a VTR 7, for example, serving as peripheral equipment and connected to the video processor body 5.

The electronic scopes 2A and 2B comprise an elongated inserting section 8 having elasticity, a thickened operating section 9 provided at a proximal end of the inserting section 8, and a universal cable 11 extending from the operating section 9 and having elasticity. The electronic scopes 2A and 2B can detachably mount a pair of connectors 12 provided on a distal end of the universal cable 11 respectively on the light source units 3A and 3B.

Further, the inserting section 8 comprises a tip 13 in which the image pickup means is received, a curving section 14 capable of being curved, formed at a rear end of the tip 13, and an elastic tube 15 formed at a rear end of the curving section 14.

One of the connectors 17 of a signal cable 16 is connected to the connector 12, whereby it is possible to detachably mount the other connector 18 on connector receipts 19A and 19B of the respective adaptors 4A and 4B.

Moreover, a recess 21 capable of receiving or accommodating the adaptors 4A and 4B are provided in a front surface of the video processor body 5. A connector receptor 23 (omitted in FIG. 1) on which the connector 22 provided on rear surfaces of the respective adaptors 4A and 4B is detachably mounted is provided within the recess 21.

The electronic scopes 2A and 2B used in the first embodiment differ from each other in their image pickup systems. One of the electronic scopes 2A has image pickup means of concurrent type for performing color image picking-up under illumination of the white light, and the other electronic scope 2B has image pickup means of surface sequential type for performing color image picking-up under sequential illuminating light of three wavelength regions.

Figure 2:
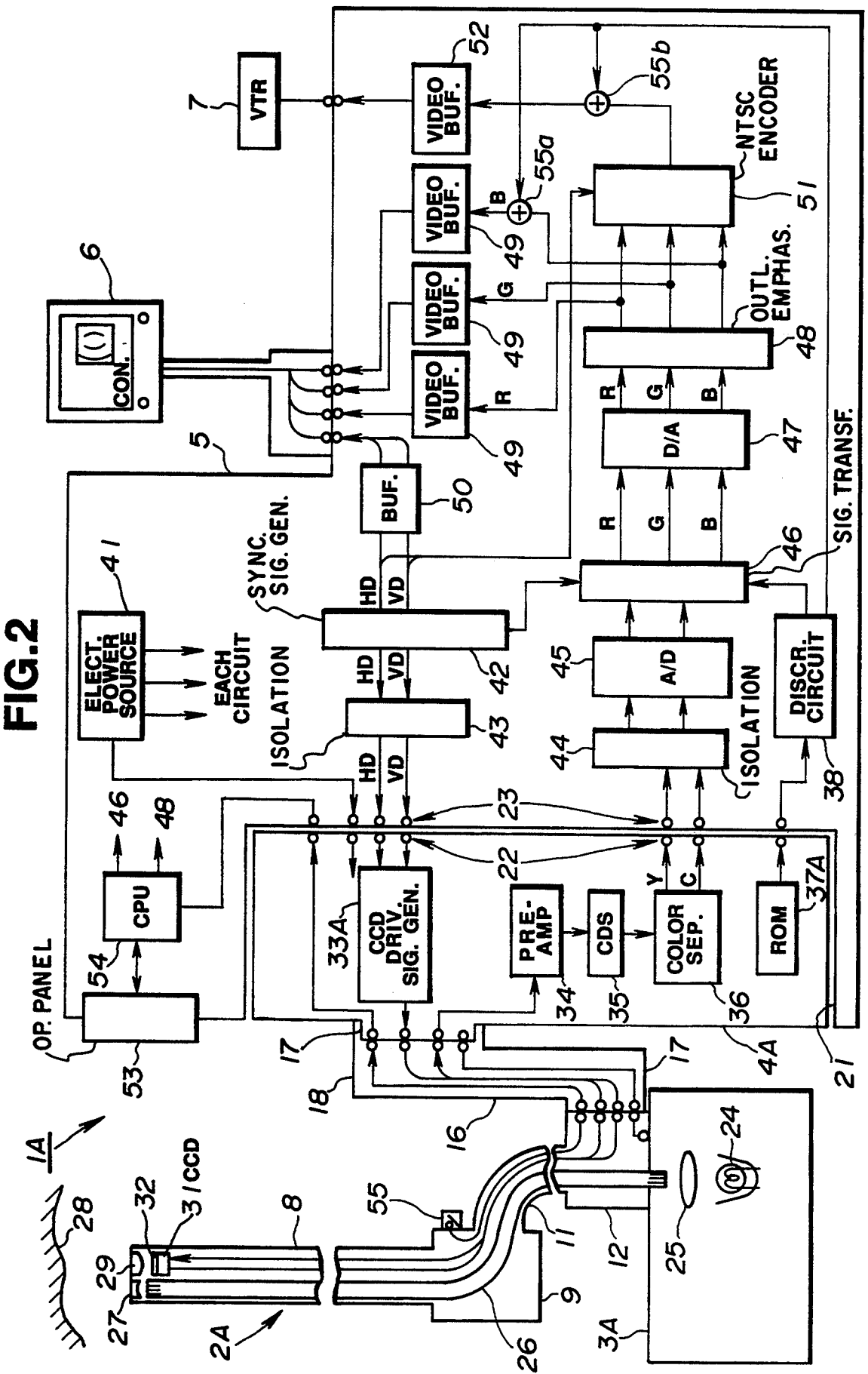

The system 1 illustrated in FIG. 1 can form an electronic endoscope system 1A of concurrent type by combination shown in FIG. 2 in a case where the system 1 is used by the electronic scope 2A of concurrent type. Moreover, the electronic endoscope system 1B of surface sequential type can be formed by combination shown in FIG. 3 in a case where the electronic endoscope system 1B is used by the electronic scope 2B of surface sequential type.

As shown in FIG. 2, a light-source lamp 24 and a condenser lens 25 are provided within the light source unit 3A. The white illuminating light radiated by the light-source lamp 24 is condensed by the condenser lens 25, and is supplied to an end face of the light guide fiber 26 at the distal end of the universal cable 11. The supplied illuminating light is transmitted to an end face adjacent to the forward end 13 of the inserting section 8, by the light guide fiber 26, and is further emanated toward a subject 28 through an illuminating lens 27 which is mounted on an illuminating window in the forward end 13.

The subject 28 illuminated by the illuminating light outgone from the illuminating window has a focal surface thereof. An optical image is focused on the photoelectric transfer surface of the CCD 31 which is arranged on the focal surface of the subject 28, by the objective lens 29 which is mounted on the observing window in the forward end 13.

A simple-plate color tip 32 of the mosaic color filter array for color separation is mounted on the photoelectric transfer surface of the CCD 31. The CCD 31 photoelectrically transfers the optical image separated in color every picture elements, by the simple-plate color tip 32.

A CCD drive-signal generating circuit 33A (referred also merely to "drive-signal generating circuit") for driving the CCD 31 on which the simple-plate color tip 32 is mounted is received within the adaptor 4A. A CCD drive signal outputted from the drive-signal generating circuit 33A is applied to the CCD 31, whereby a photoelectrically transferred image signal is read out. Furthermore, preprocess processing means for performing preprocess processing with respect to the CCD output signal is received within the adaptor 4A to be described subsequently.

That is, the COD output signal is amplified by a pre-amplifier 34 which is received within the adaptor 4A and, subsequently, is inputted into a CDS circuit 35. Unnecessary signals such as a transmitting clock carrier and the like are removed. Thus, an image signal component is separated and is extracted.

An output signal from the CDS circuit 35 is inputted to a color separating circuit 36, and is color-separated into a luminance or intensity signal Y and a color signal C (more specifically, the color signal represents a color difference signal R-Y/B-Y) which are inputted into a video processor body 5 which functions as a common signal processing system.

Further, a ROM 37A is received within the adaptor 4A. The ROM 37A houses or stores information for driving the CCD 31 which forms image pickup means which is connected to the adaptor 4A and which is used, and information for performing signal processing adapted for an image signal outputted from the adaptor 4A.

The adaptor 4A is mounted on the video processor body 5, whereby the information of the ROM 37A is read out by a judging circuit 38 within the video processor body 5, and is used for signal processing within the video processor body 5.

The video processor body 5 receives therein a power source 41. Power source is supplied from the power source 41 respectively to the secondary circuit systems (various circuits thereof) within the video processor body 5. The power source 41 is provided also with a power source for a secondary circuit system and an isolated power source for a patient circuit system. The power source 41 supplies the power source for the patient circuit system to the adaptor 4A to operate circuits for patient circuit system within the adaptor 4A (that is, the drive-signal generating circuit 33A ~ the color separating circuit 36. In this connection, the ROM 37A belongs to the secondary circuit system, and is supplied with driving power source from the power source for the secondary circuit system (illustration omitted)).

A synchronous signal generator 42 received within the video processor body 5 generates horizontal and vertical synchronous signals HD and VD, and supplies them to the CCD drive-signal generating circuit 33A within the adaptor 4A, through a first isolation circuit 43. By these synchronous signals HD and VD, the CCD drive-signal generating circuit 33A generates exclusive drive pulses which drive the CCD 31 of concurrent type (the CCD 31 provided with the color tip 32).

The intensity signal Y and the color signal C outputted from the color separating circuit 36 are isolated and separated from the patient circuit system through a second isolation circuit 44, and is inputted to an A/D conversion circuit 45 which forms a secondary circuit system. After the intensity signal Y and color signal C have been converted to a digital signal, the intensity signal Y and the color signal C are inputted to the signal conversion circuit 46.

Figure 4:
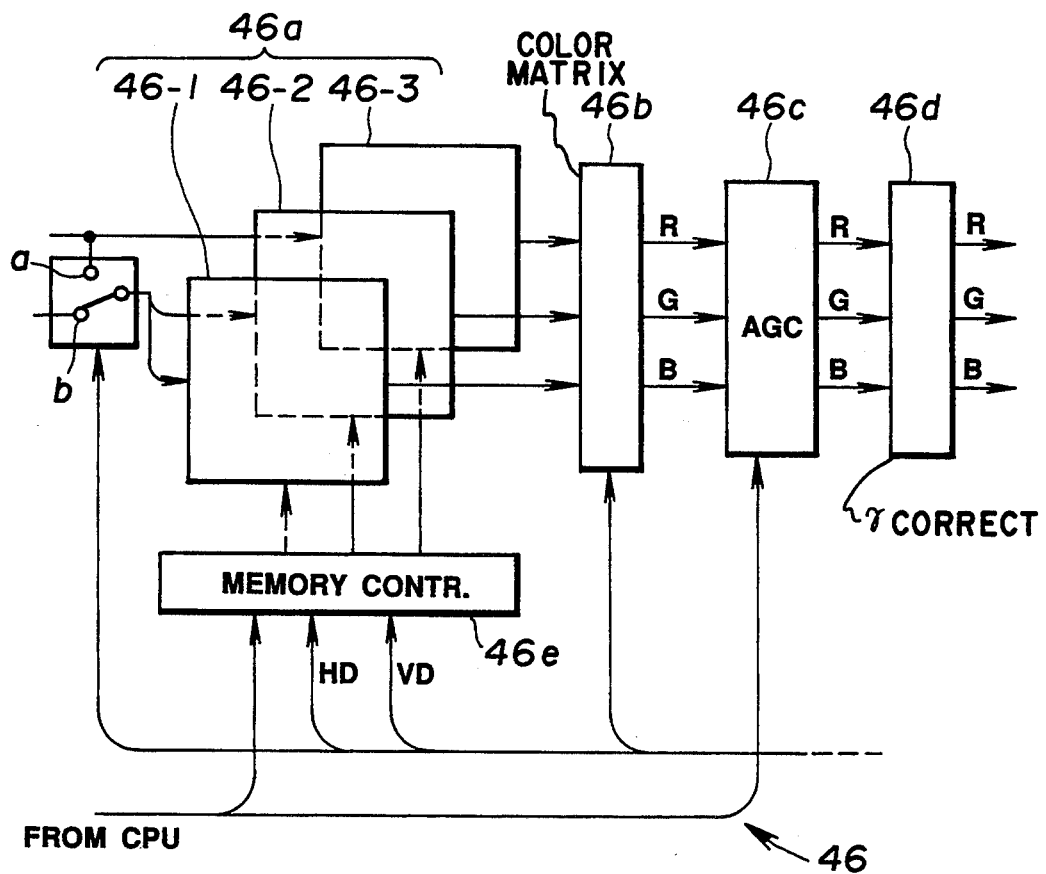

As shown, for example, in FIG. 4, the signal conversion circuit 46 comprises a memory 46a (three memories 46-1, 46-2 and 46-3) used for coincidence of the image signal, display of a freeze image and the like, a color matrix conversion circuit 46b for performing conversion to an RGB signal, an AGe circuit 46c for performing AGC processing, a gamma correction circuit 46d for performing gamma correction, a memory controller 46e for controlling writing/reading-out with respect to the memory 46a, and a switch 46f for selecting a signal inputted to the memories 46-2 and 46-3. The signal conversion circuit 46 performs signal conversion processing with respect to the inputted signal, to output an RGB signal.

The switch 46f is arranged such that, in a case of the concurrent type, a contact b is selected as shown in FIG. 4 so that the color-difference signal R-Y/B-Y is inputted to the memories 46-2 and 46-3, while, in a case of the surface sequential type, a contact a is selected so that the R, G and B signals are inputted to the three memories 46-1, 46-2 and 46-3.

The memory 46a has a memory capacity corresponding to a signal for one frame of the color image in a case of the surface sequential type, while, in a case of the concurrent type, the number of picture elements corresponding to one frame of the color image becomes a third of that in a case of the surface sequential type. Accordingly, writing to the memory portion 46a and reading-out from the memory portion 46a are performed by assignment of a memory address corresponding to the reduced number of picture elements mentioned above.

Moreover, the color matrix conversion circuit 46b outputs the inputted signal without being converted by through, since the inputted signal has already been brought to the RGB signal, in a case of the surface sequential type.

In a case where the RGB signal is generated, judging information of the judging circuit 38 is used to control the switch 46f and the color matrix conversion circuit 46b.

The RGB signal outputted from the signal conversion circuit 46 is converted to an analog signal by a D/A conversion circuit 47 and, subsequently, an outline component of the signal is emphasized by an outline emphasizing circuit 48. The RGB signal emphasized in outline is arranged such that a standard image signal is outputted to an outside monitor 6 together with the synchronous signal through the buffer circuit 50, through the video buffer circuit 48. The color monitor 6 displays the subject image in color.

In connection with the above, the B-signal emphasized in outline, for example, is mixed with index information judged by the judging circuit 38 so that index information (for example, the fact that the scope is a concurrent type, or kinds or types of the adaptor 4A) on the color monitor 6.

Furthermore, the RGB signal corrected in outline is inputted in the encoder 51 together with the synchronous sisal, and is converted to an image signal of an NTSC system. The image signal of the NTSC system is also inputted to a VTR 7, for example, through a video buffer 52, and the image signal is recorded.

In connection with the above, the output from the encoder 51 is also mixed with the index information of the judging circuit 38 by the adding circuit 55b, and is outputted.

Further, the video processor body 5 has, for example, a front surface thereof which is provided with an operation panel 53. The operation panel 53 is provided with switch buttons for setting a tone of image, an amount of outline emphasis and the like so as to be suited for operator's liking or taste, or the like. An operating signal in a case where the operation panel 53 is operated is inputted to a CPU 54.

The CPU 54 can discriminate an operating signal to change operating the condition/operating characteristic of the signal conversion circuit 46 and the outline emphasizing circuit 48. In a case where operation to change the tone is performed, the CPU 54 changes the characteristic of the AGC circuit 46c in FIG. 4, for example, to change the tone.

Moreover, an ON-signal which operates the freeze switch 55 of the electronic scope 2A is inputted to the CPU 54 through the adaptor 4A. When the CPU 54 detects the ON-signal, the memory portion 46a forming the signal conversion circuit 46 is set under a freeze condition, to control the memory portion 46a so as to output the frozen image signal toward the monitor 6. In this case, the CPU 54 outputs a control signal of writing inhibition to the memory portion 46a, with respect to the memory controller 46e.

The memory controller 46e applies a write de-enable signal to the memory portion 46a. The memory 46a holds or retains an image prior to the write de-enable signal. The held is repeatedly displayed as a still picture on the monitor 6.

Figure 3:
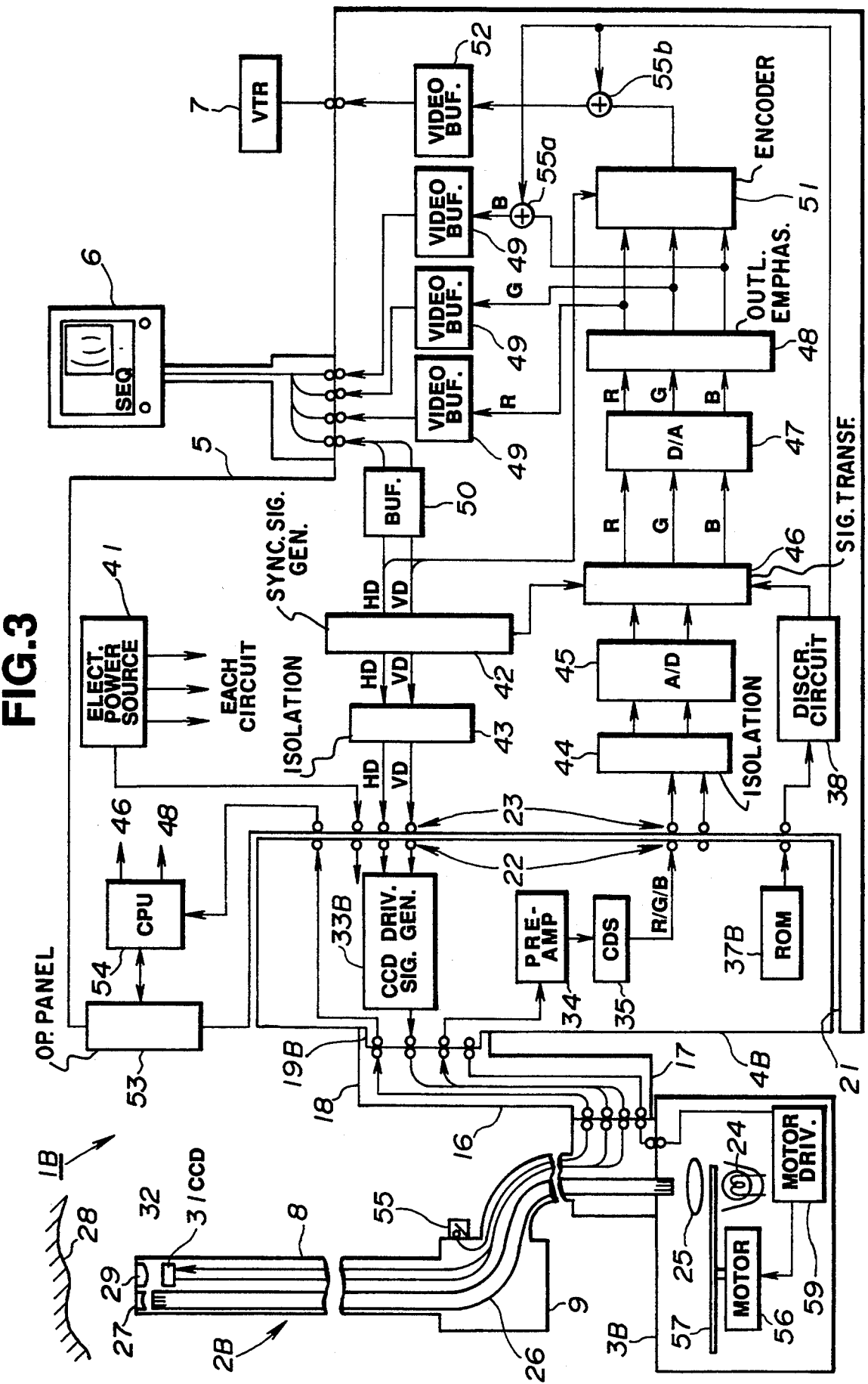

On the other hand, in a case where the electronic scope 2B of surface sequential type is used, the arrangement is brought to an arrangement of the electronic endoscope system 1B of surface sequential type illustrated in FIG. 3.

The electronic scope 2B of surface sequential type uses a CCD 31 having no single-plate color tip 32 in the electronic scope 2A of concurrent type illustrated in FIG. 2. That is, a photodiode array and a transmitting part which are brought to a photoelectric transferring portion are the same in structure as each other and, accordingly, can be driven by drive signals substantially the same as each other. In the present embodiment, as the CCD 31, for example, an interline transmitting type is employed or adopted.

Furthermore, in the light source unit 3A illustrated in FIG. 2, the light source unit 3B is arranged such that a color filter disc 57 driven in rotation by a motor 56 is arranged in an illuminating light path between the lamp 24 and the lens 25.

Figure 5:
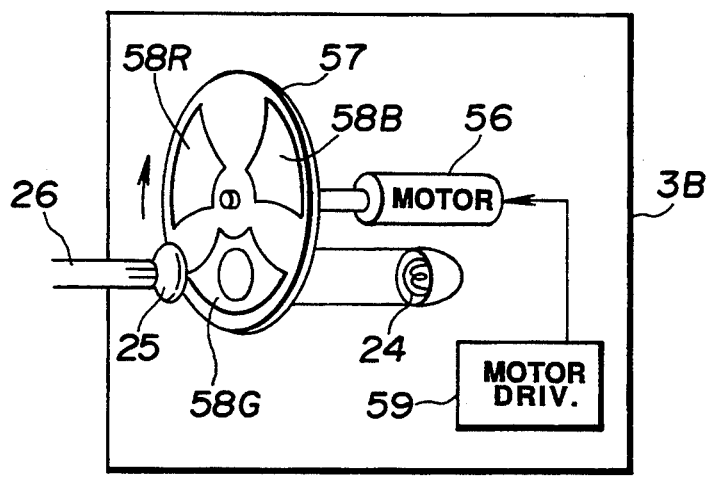

As shown in FIG. 5, R, G and B transparent filters 58R, 58G and 458 for transmitting light of R, G and B in a peripheral direction of the disc are mounted respectively on the color filter disc 57. The R, G and B transparent filters 58R, 58G and 58B are interposed successively in the illuminating light path to supply surface sequential light of R, G and B to the light guide 26.

In connection with the above, the motor 56 is so controlled as to be rotated with constant rotational speed by a motor drive circuit 59. Moreover, a vertical synchronous signal VD is applied to the motor drive circuit 59 from the synchronous signal generator 42 which is received within the video processor body 5, through the adaptor 4B. The motor 56 is rotatively driven in synchronism with the vertical synchronous signal VD.

Figure 6:
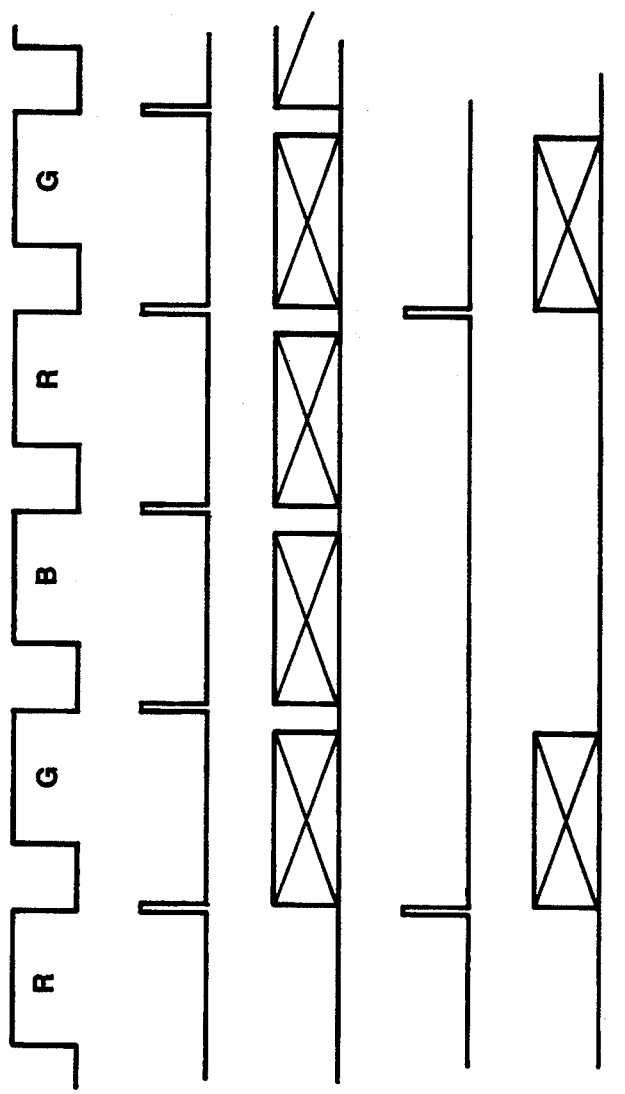

Both the electronic scopes 2A and 2B of concurrent type and surface sequential type are arranged such that, in a case where the CCD 31 is interline transmission type, the drive signal generating circuit 33B within the adaptor 4B generates a transmitting signal TS illustrated in FIG. 6b at completion of the illuminating periods of time of R, G and B illustrated in FIG. 6a, for example, and transmits the transmitting signal TS to adjacent vertical transmitting resistors. Subsequently, the drive signal generating circuit 33B applies vertical and horizontal transmitting signals $\phi V$ and $\phi H$ illustrated in FIG. 6c to the CCD 31. The vertical transmitting signal $\phi V$ and the horizontal transmitting signal $\phi H$ are outputted only by the number of vertical picture elements and the number of horizontal picture elements.

In a case of concurrent type, the transmitting signal TS is brought to one illustrated in FIG. 6c, and the vertical and horizontal transmitting signals $\phi V$ and $\phi H$ are brought to ones illustrated in FIG. 6e. Accordingly, a case of surface sequential type becomes one-third the cycle of the case of concurrent type. Thus, the CCD drive-signal generating circuit 33A of concurrent type should generate the vertical and horizontal transmitting signals $\phi V$ and $\phi H$ only during the above-mentioned one-third period of time, in the transmitting signal generating circuit in the CCD drive-signal generating circuit 33B in a case where the CCD drive signal generating circuit 33A is surface sequential type, for example (for example, the vertical and horizontal transmitting signals $\phi V$ and $\phi H$ are generated only during this one-third period of time and, subsequently, generation is inhibited until next or subsequent transmitting signal TS). Alternatively, the arrangement may be such that a three-dividing circuit for performing division by three is added, and the horizontal transmitting signals $\phi V$ and $\phi H$ are generated only by the number of vertical and horizontal picture elements by an output from the three-division circuit.

In this manner, if the common CCD 31 is adopted, parts capable of being held in common by the two CCD drive-signal generating circuits 33A and 33B can increase so that the cost can be reduced.

As shown in FIG. 3, the output signal from the CCD 31 passes through the preamplifier 34 and the CDS circuit 35, and is brought to R/G/B signals of time series (serial). That is, the output from the CCD 31 is brought to the R/G/B signals generated under the illuminating light in the respective wavelength areas or regions. The R/G/B signals pass through a signal line of a single network or system, and is inputted to the isolation circuit 44 within the video processor body 5 (in a case of the concurrent type, two systems).

In a case of a surface sequential type, the other signal line is not used for signal transmission. The signal isolated by the isolation circuit 44 is inputted to the A/D conversion circuit 45. The signal isolated by the isolation circuit 44 is then A/D-converted and, subsequently, is inputted to the signal conversion circuit 46.

By the judging signal of the judging circuit 38 for judging the information of the ROM 37B, the serial R/G/B signals are successively stored in the memories 46-1, 46-2 and 46-3 at the signal conversion circuit 46. The stored R, G and B signals are simultaneously read out and are coincided with each other. The stored R, G and B signals pass through the color matrix conversion circuit 46b, pass through the AGC circuit 46c and the Y correction circuit 46d and are converted to analog RGB signals by the D/A conversion circuit 47.

FIG. 2 is applicable to a case on and after the D/A conversion circuit 47. In this connection, the index information displayed on the color monitor 6 is different from that in FIG. 2.

According to the first embodiment of the invention, only detachment and replacement of the adaptors 4A and 4B makes it possible to cope with the electronic scopes 2A and 2B of concurrent type and surface sequential type by the common video processor body 5, and it is made possible to display the image signal generated by signal processing, on the color monitor 6.

That is, it is possible to selectively use the systems of the concurrent type and surface sequential type in accordance with using circumstances and the like, and it is possible to perform adequate endoscope inspection. For example, in a case where a large movement or motion is observed, if the system of concurrent type is used, there can be produced an image having no color shear. On the other hand, if the surface sequential type is adopted with respect to a portion having less motion, there can be produced an endoscope image having high resolution of the order of three times even if the CCD having the number of picture elements the same as these of the concurrent type is used. Thus, it is possible to discriminate fine detail.

Moreover, the embodiment has an advantage that a desired system can be arranged at low cost. Operation becomes easier than a case where the signal processing unit is not divided into an adaptor and a video processor unit, and a case where the signal processor unit is reconnected to form a system of different image pickup systems.

The background in which the electronic scopes 2A and 2B of the concurrent type and the surface sequential type are used properly will further be described.

For example, in a case where the electronic scope is used in clinic, clinic is performed by the use of the electronic scope of concurrent type having wide usage as an electronic scope for a routine first inspection. However, depending upon cases, a case occurs frequently in which biopsy picking or collection and various kinds of handling (for example, where a polyp is cut off by forceps, and handling is performed by an electric surgical knife and a laser.) additionally continues.

In such a case, it is required to replace through bores (channel) for a manipulator of the electric scope and for forceps with ones having a large opening diameter. Upon replacement, since the CCD small in size is used in order that the electronic scope is brought to an electronic scope having the same outer diameter, the number of picture elements of the CCD is reduced. Thus, resolution is reduced, or a picture area is reduced so that observation at the same quality (the same picture quality) is made impossible. In this case, it is preferable that the electronic scope of surface sequential type is used whereby there can be produced picture quality the same in quality even with fewer picture elements.

In view of the above, if it is required to replace also the video processor body, it is required that connections between the video processor body and peripheral instruments such as the monitor 6, the VTR 7, a photographing unit and the like are all tried again. Thus, this is very time-consuming.

In this case, it will be considered that two video processors for concurrent type and for surface sequential type are prepared, and a peripheral instrument and a switch capable of switching a connecting condition at a time are used. However, it is uneconomical in view of money and in view of a space to prepare the two video processors. This is because, as will be seen if the interior of the video processor body 5 shown in FIG. 2 or FIG. 3 is looked or seen, there are very many blocks used commonly. Particularly, the isolation and a power-source circuit in which a patient circuit and a secondary circuit which are peculiar to medical instruments are distinguished from each other are blocks in which an occupied area and weight are high.

Moreover, a synchronous-signal generating circuit for exposing pictures on the monitor and various peripheral image instruments, and a video buffer, various image signal proceedings (Y, AGC, outline emphasis) including the interfaces of A/D and D/A, and the like are expensive blocks, including also the electronic scope.

On the other hand, according to the present embodiment, only replacement of the adaptors 4A and 4B and the light-source units 3A and 3B makes it possible to cope with the above-described problem. Accordingly, there is a reduction in wasted time therefore reducing the economical burden.

In this embodiment, parts which can be used commonly remain in the video processor body 5, universal replacement or compatibility and utilization make it easier to use the video processor body 5 and similar function can be realized with less economical burden.

Furthermore, the adaptor portion and the video processor portion are formed separate from each other, whereby expansion of the function is made easier than a case of integrality.

Figure 7:
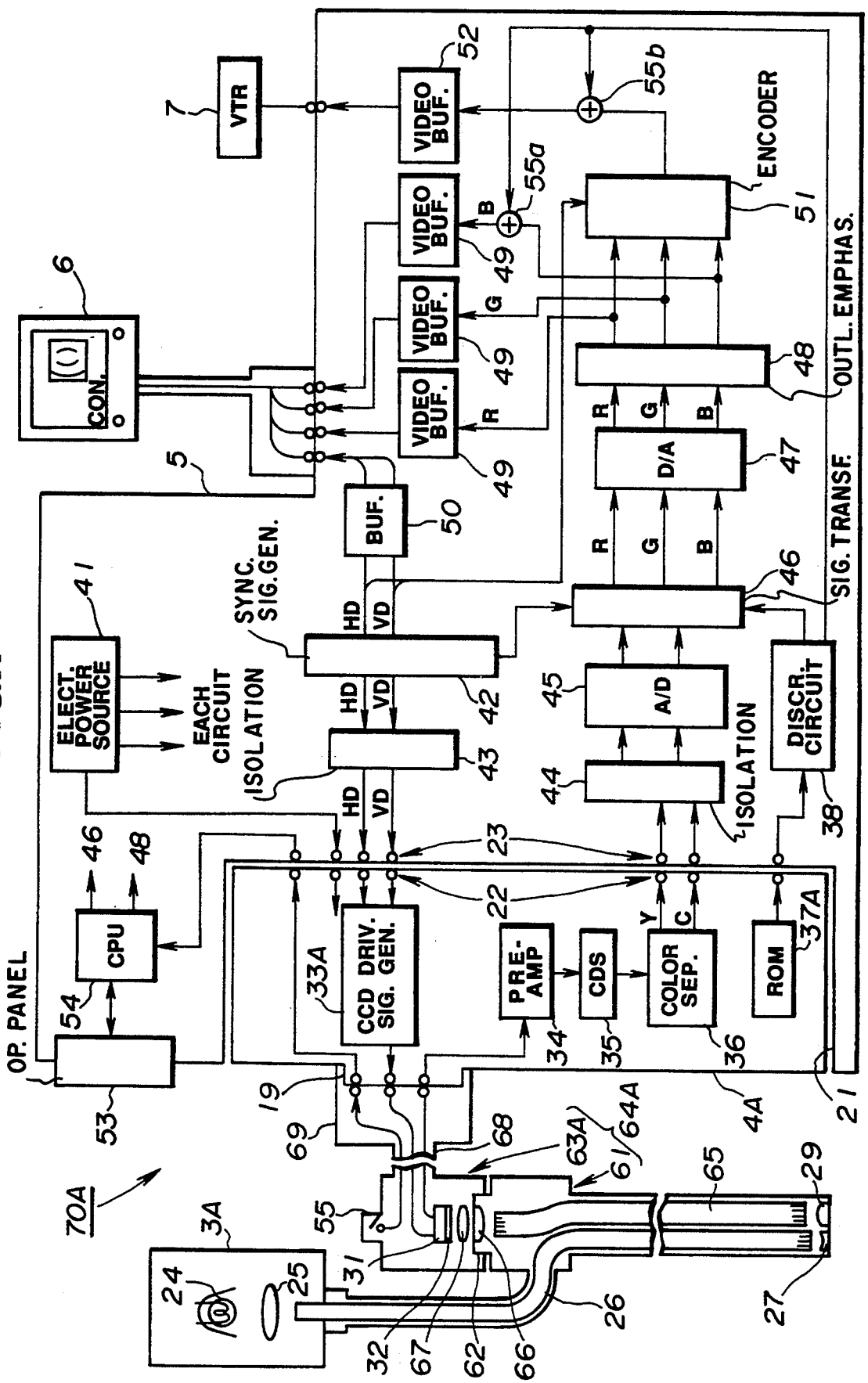
FIG. 7 is a block diagram showing an arrangement of an endoscope system of concurrent type according to a first modification of the first embodiment.

A first modification of the first embodiment will next be described. In addition to the arrangement of the first embodiment, the first modification can use a TV camera mounting scope 64A in which a TV camera 63A is mounted on an ocular portion 62 of a fiber scope 61, further as shown in FIG. 7.

The fiber scope 61 is arranged such that, in the electronic scope 2A of concurrent type illustrated in FIG. 2, one of end surfaces of the image guide 65 is arranged on a focal surface of the objective lens 29, and imaged optical image is transmitted to an end surface adjacent to the ocular portion 62. The transmitted optical image can be observed in enlargement by the ocular lens 66. Further, the fiber scope 61 is provided with a light guide 26 similarly to the electronic scope 2A of concurrent type. The light guide 26 can be mounted on the light-source unit 3A.

In a case where the TV camera 63A is mounted on the ocular portion 62, the transmitted optical image is imaged on the CCD 31 further through the imaging lens.

In the TV camera 63A, the simple-plate color tip 32 is mounted on a front surface of the CCD 31. The CCD 31 photoelectrically transfers the optical image separated in color every picture elements by the simple-plate color tip 32. The signal cable 68 extending out from the TV camera 63A has a distal end thereof on which a connector 69 is provided. The connector 69 can be connected to a connector receptor 19.

The TV-camera mounting scope 64A has a function similar to that of the electronic scope 2A of concurrent type. In FIG. 2, the TV-camera mounting scope 64A is substituted for the electronic scope 2A of concurrent type, to be capable of forming an endoscope system 70A of concurrent type. The same or identical reference numerals are applied to the elements or constitutional elements described with reference to FIG. 2, and the description thereof will be omitted. Function of the first modification is substantially similar to that of the first embodiment. Further, according to the first modification, it is possible to widely select and utilize the system arrangement in case where inspection is performed.

In the TV camera 63A illustrated in FIG. 7, the simple-plate color tip 32 is mounted on the front surface of the CCD 31. Accordingly, in a case where the TV camera 63A is mounted on the fiber scope 61, the TV camera 63A can be used similarly to the electronic scope 2A of concurrent type.

On the other hand, in the TV camera 63A illustrated in FIG. 7, in a case where the simple-plate color tip 32 is not mounted on the front surface of the CCD 31, the TV camera has a function the same as that of the electronic scope 2B of surface sequential type, and can be used similarly to the electronic scope 2B of surface sequential type.

A second modification of the first embodiment will next be described. The second modification is arranged such that, in the first embodiment, light-source units are received respectively within the adaptors 4A and 4B.

Figure 8:
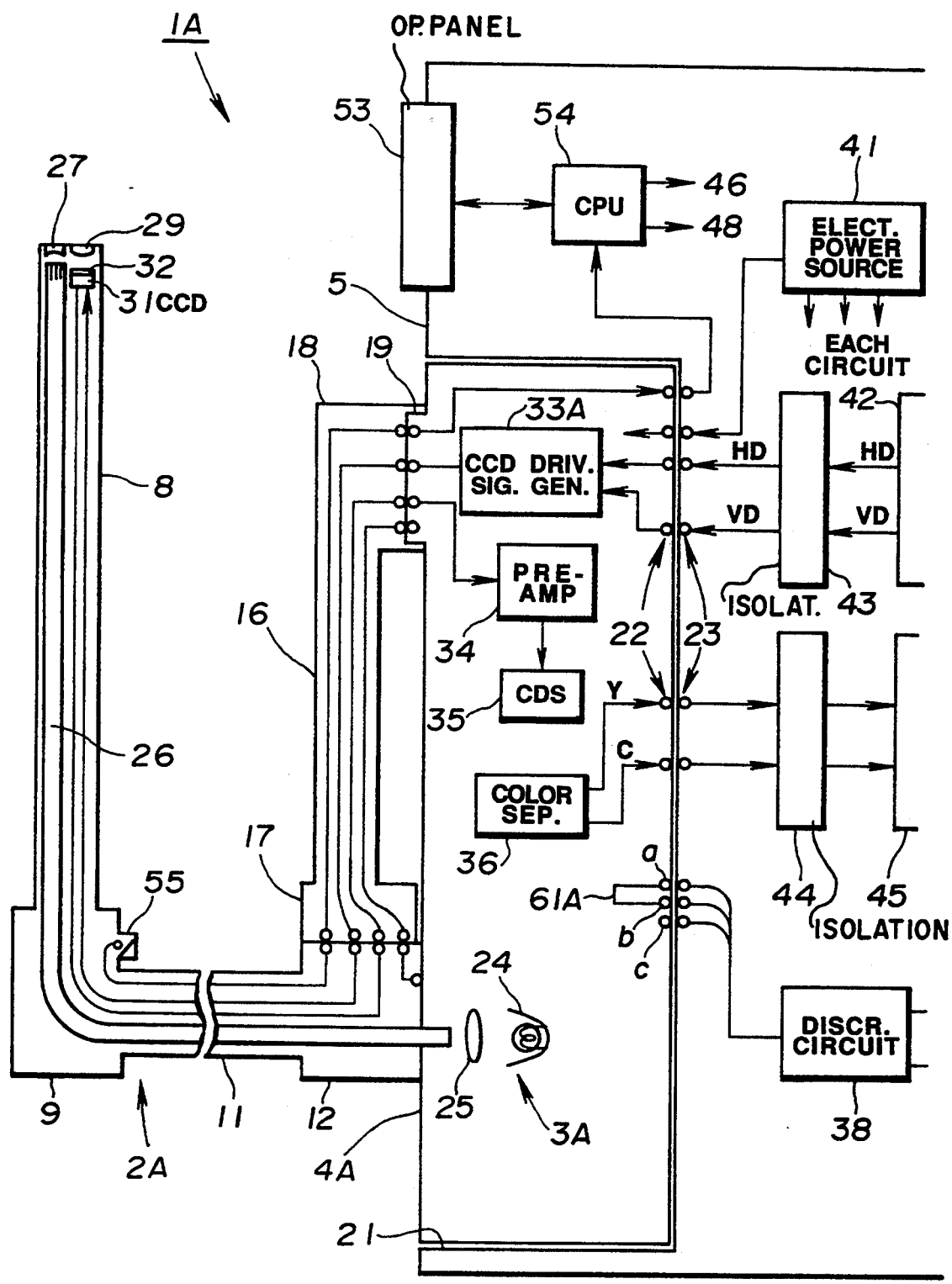
FIGS. 8 and 9 relate to a second modification of the first embodiment, FIG. 8 being a block diagram showing a principal portion of an electronic endoscope system of concurrent type.

As shown in FIG. 8, the light-source unit 3A illustrated in FIG. 2 is received within the adaptor 4A in a case of the electronic endoscope system 1A of concurrent type. Moreover, in the modification, two contacts a and b of, for example, the three contacts a, b and c are conducted to each other by a lead wire R, in place of the ROM 37A. The judging circuit 38 detects conduction between the two contacts a and b to output a judgment signal for performing signal handling of the concurrent type. Other arrangements are the same as those illustrated in FIG. 2.

Figure 9:
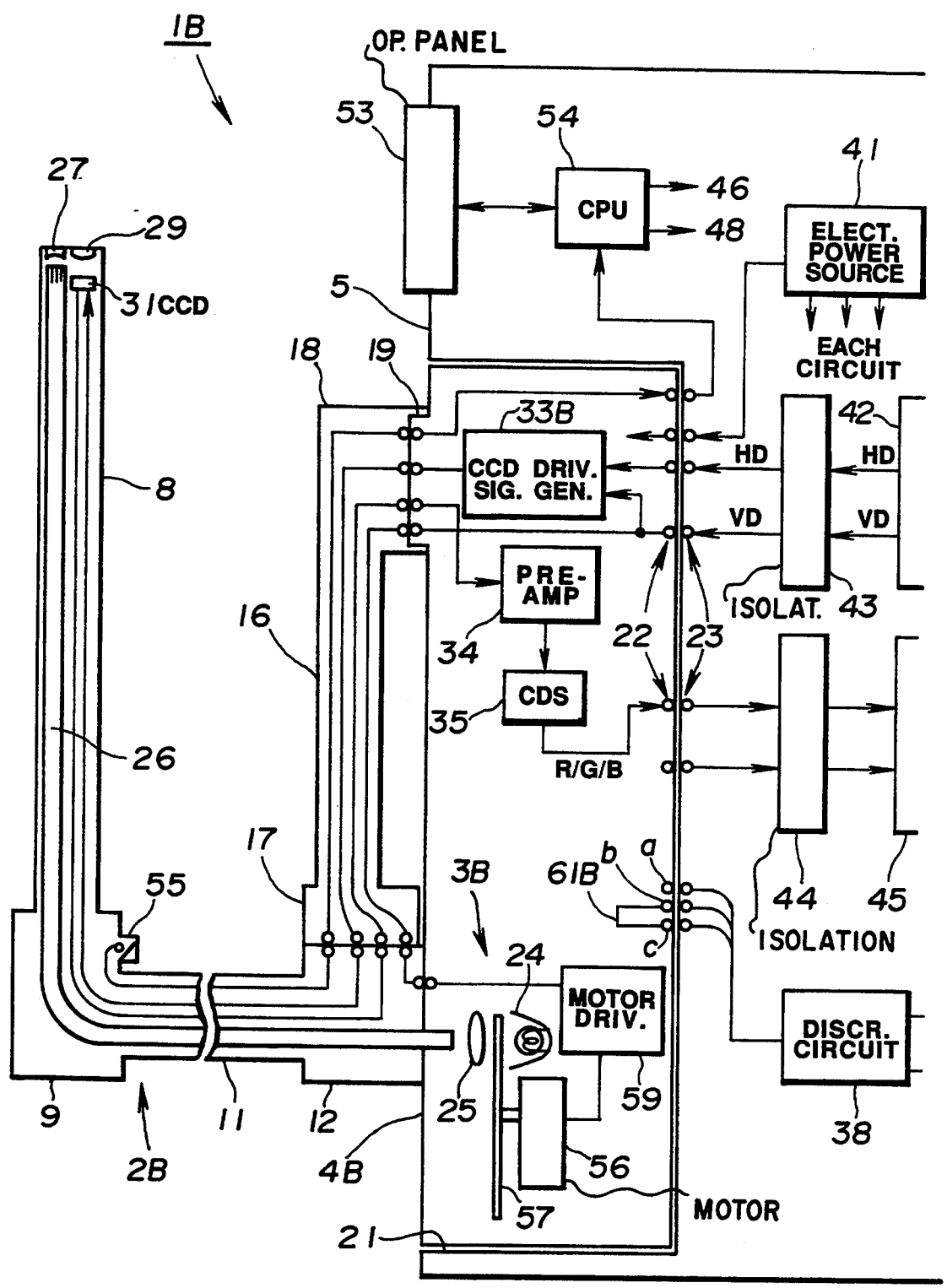

The light-source unit 3B illustrated in FIG. 3 is received within the adaptor 4B in a case of the electronic endoscope system 1B of surface sequential type illustrated in FIG. 9. Furthermore, in the modification, the two contacts b and c of the three contacts a, b and c, for example, are conducted to each other by the lead wire R in place of the ROM 37B. The judging circuit 38 detects conduction of the two contacts b and c to output a judgment signal for performing signal handling of surface sequential type. Other arrangements are the same as those in FIG. 3.

In connection with the above, the lamp 24 may use a xenon amp, a halogen lamp, a metal halide lamp. Alternatively, an LED of high intensity may be used to miniaturize the adaptors 4A and 4B.

The modification has a function and advantages substantially the same as those of the first embodiment.

Figure 10A:
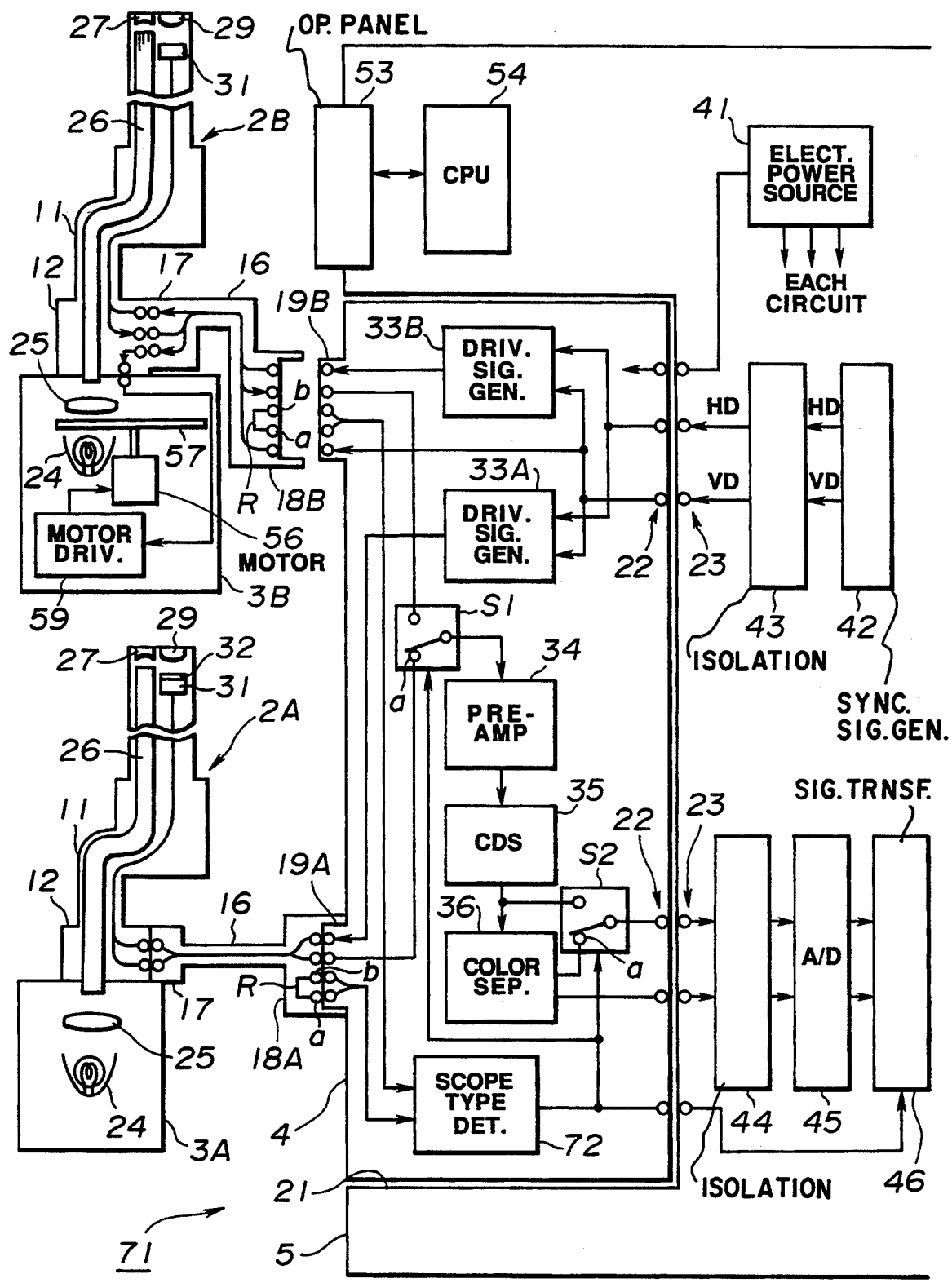
FIG. 10a is an arrangement view of a principal portion of an electronic endoscope system according to a second embodiment of the invention.

FIG. 10a shows an arrangement of a principal portion of an electronic endoscope system 71 according to a second embodiment of the invention. In the first embodiment, the exclusive adaptors 4A and 4B corresponding respectively to the electronic scope 2A of concurrent type and the electronic scope 2B of surface sequential type have been adopted. However, the present embodiment uses a single adaptor 4 having functions of the pair of adaptors 4A and 4B, to form the electronic endoscope system 71.

The adaptor 4 can detachably be mounted on a video processor body 5. The adaptor 4 has built therein a drive-signal generating circuit 33A of concurrent type and a drive-signal generating circuit 33B of surface sequential type, for example. Further, the adaptor 4 has a pair of connector receipts 19A and 19B. A connector 18A connected to the electronic scope 2A of concurrent type and a connector 18B connected to the electronic scope 2B of surface sequential type can be connected respectively to the connector receipts 19A and 19B.

A drive signal can be applied to a CCD 31 through the connected connector 18A or 18B, and a read-out CCD output signal can be outputted toward an isolation circuit 44 within the video processor body 5 through a change-over switch S1, a preamplifier 34, a CDS circuit 35, a color isolation circuit 36 and the change-over switch S1.

In the present embodiment, pins a and b for detecting scope connection are provided respectively on the connectors 18A and 18B, and are respectively short-circuited to the connectors 18A and 18B through lead wires R. A scope-connection detecting circuit 72 for detecting scope connection and kinds or types thereof depending upon the fact as to whether any of the pins a and b is short-circuited is housed or received within the adaptor 4.

When the pins a and b adjacent to the connector receptor 19A are short-circuited, the scope-connection detecting circuit 72 judges that the electronic scope 2A of concurrent type is connected, to select a signal processing system corresponding to the concurrent type. On the other hand, when the pins a and b adjacent to the connector receptor 19B are short-circuited, the scope-connection detecting circuit 72 judges that the electronic scope 2B of surface sequential type is connected, to select a signal processing system corresponding to the surface sequential type.

In a case of FIG. 10a, since the pins a and b adjacent to the connector receipt 19A are short-circuited, the scope-connection detecting circuit 72 selects the change-over switch S1 to a side adjacent to the contact a, guides or leads an output signal from the electronic scope 2A of concurrent type to the preamplifier 34, selects the change-over switch S2 also to a side of the contact a, and leads a signal passing through the color isolation circuit 36, toward the isolation circuit 44.

A scope-connection detecting signal from the scope-connection detecting circuit 72 is inputting also to a signal conversion circuit 46 within the video processor body 5, and performs a function substantially similar to that of the first embodiment. In the present embodiment, there is a merit that it is dispensed with to replace the adaptor 4.

In the present second embodiment, also in a case of the concurrent type and the surface sequential type, the common adaptor 4 is used.

Figure 10C:
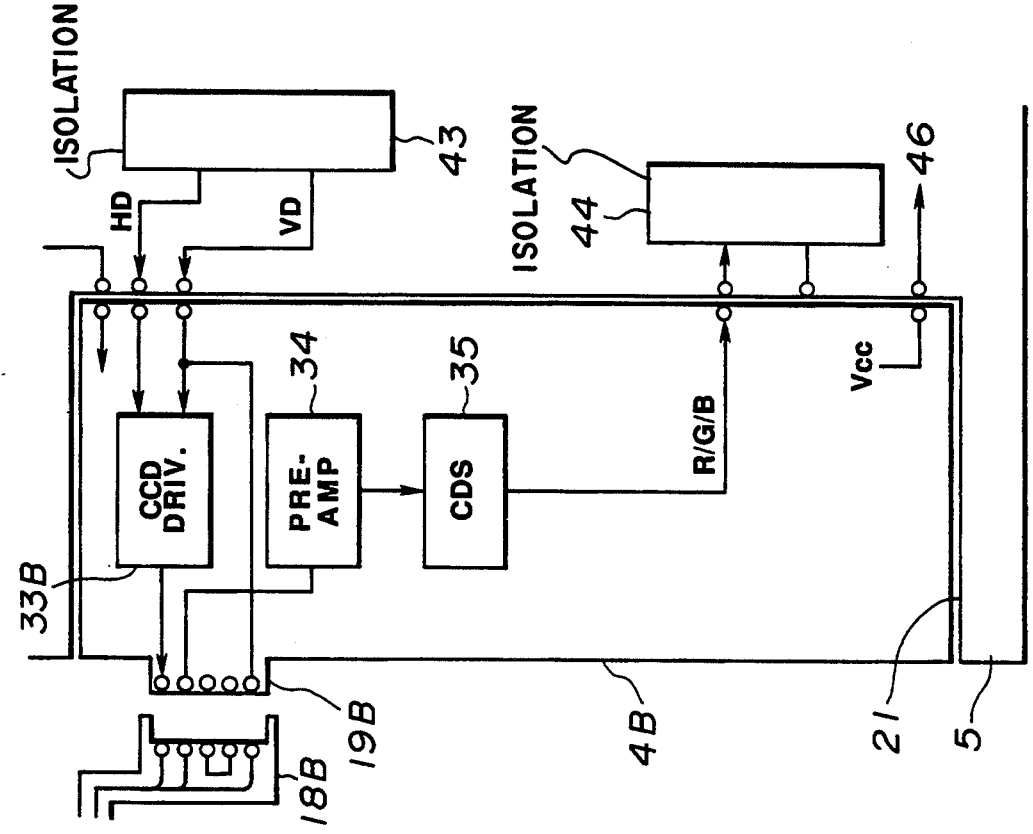
FIGS. 10b and 10c are arrangement views respectively showing principal portions of electronic endoscope systems of surface sequential type and of concurrent type, according to a modification of the second embodiment of the invention.
Figure 10B:
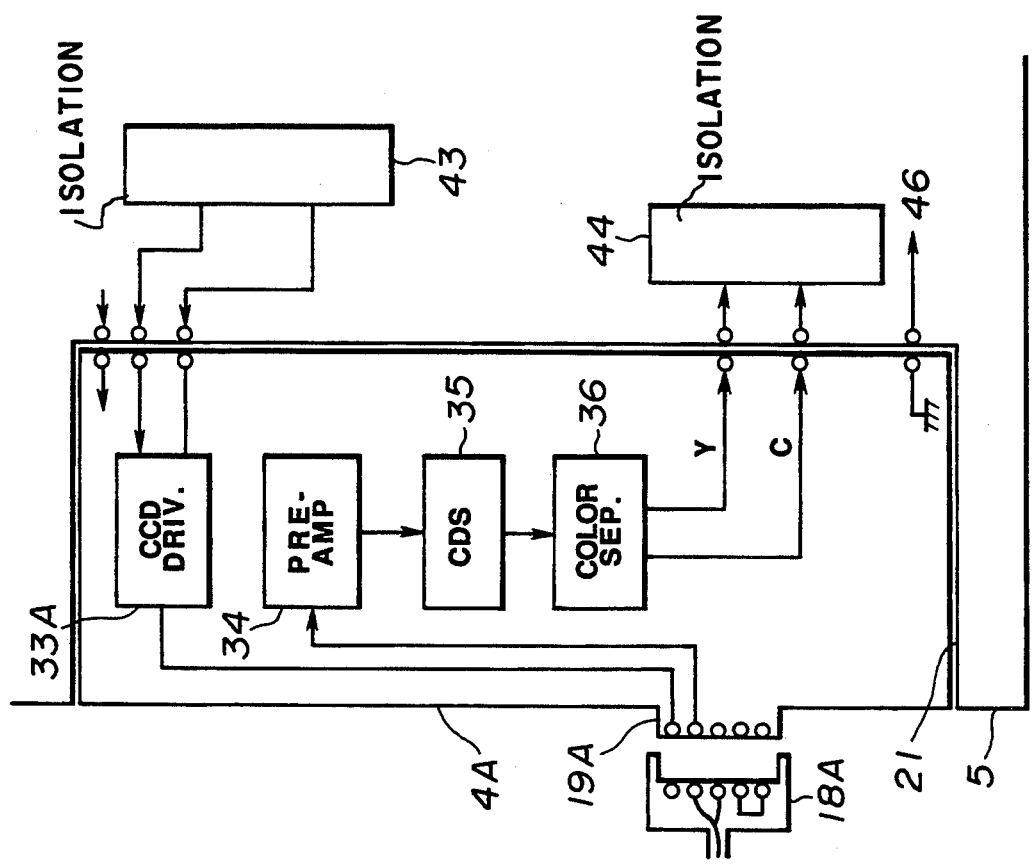

On the other hand, the arrangement may be such that, by selection of a user, the exclusive adaptors 4A and 4B are respectively used in a case of the concurrent type and the surface sequential type as shown in FIG. 10b and FIG. 10c, or the common adaptor 4 can be used as shown in FIG. 10a.

In FIG. 10b, because of the adaptor 4A to which the electronic scope 2A of concurrent type is connected, the scope connection detection is not performed, but it is possible to send a discrimination signal of "L" toward the video processor body 5 in a case where the adaptor 4A is mounted on the video processor body 5. The signal circuit 46 within the video processor body 5 performs signal conversion processing with respect to the electronic scope 2A of concurrent type, by the discrimination signal of "L".

Similarly, scope connection detection is not performed also by the adaptor 4B shown in FIG. 10c, but, in a case where the adaptor 4B is mounted on the video processor body 5, a discrimination signal of "H" can be sent toward the video processor body 5. The signal conversion circuit 46 performs signal conversion processing with respect to the electronic scope 2B of surface sequential type, by the discrimination signal of "H". Others are the same in arrangement as those illustrated in FIG. 10a.

According to the modification, it is possible for the user to widen selective width of the system arrangement. For example, in a case where only one of image pickup systems is much used, the system arrangement illustrated in FIG. 10b or FIG. 10c is adequate. On the other hand, in a case where two image pickup systems are both used frequently, the system illustrated in FIG. 10a is adequate in which replacement of the adaptor 4 is not required with respect to the two image pickup systems.

A third embodiment of the invention will next be described. The embodiment is of structure in which an adaptor to which an electronic scope is connected is further connected to a video processor body through a light-source unit.

Figure 11:
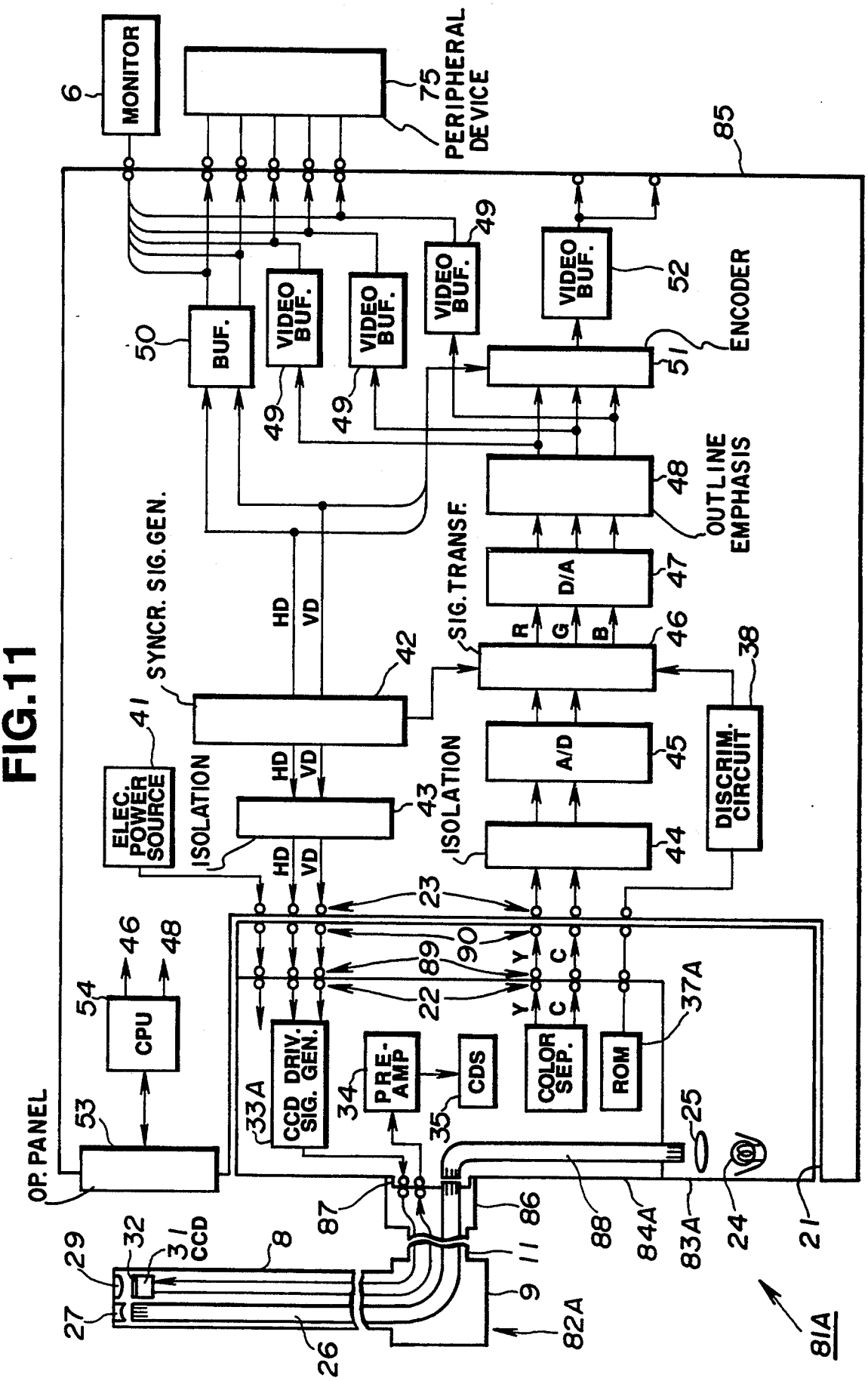
FIGS. 11 and 12 relate to a third embodiment of the invention, FIG. 11 being a block diagram showing an arrangement of an electronic endoscope system of concurrent type, according to the third embodiment of the invention.

In an electronic endoscope system 81A of concurrent type, illustrated in FIG. 11, according to the third embodiment of the invention, an electronic scope 82A of concurrent type is connected to an adaptor 84A. The adaptor 84A is connected to a light-source unit 83A. Moreover, the light-source unit 83A is connected to a video processor body 85.

A connector 86 in which a connector for light source and a connector for signal are integrated with each other is provided at a distal end of a universal cable 11 of the electronic scope 82A. The connector 86 is connected to a connector receipt 87 for light source and for signal of the adaptor 84A. The electronic scope 82A has a light guide 26 which is connected to a light-guide connector receptor of the light-source unit 83A through the light guide 88 within the adaptor 84A. The light guide 88 has an end surface thereof to which illuminating light is supplied from the light-source unit 83A.

A connector 22 adjacent to a rear surface of the adaptor 83A is connected to a connector receptor 89 at a front surface of the light-source unit 83A. The connector receptor 89 is conducted to a connector 90 adjacent to the rear surface through a lead wire. The connector 90 is the same in shape or configuration as the connector 22, and is connected to a connector receipt 23 of the video processor body 85.

In connection with the above, in the present embodiment, two of an RGB output terminal and an NTSC output terminal are provided, for example, and a color monitor 6 is connected to one of the RGB output terminals, while peripheral units 75 such as a recording unit and the like are connected to the other RGB output terminal, for example. The same or identical reference numerals are applied respectively to constitutional elements or components the same as those described with reference to the first embodiment, and the description thereof will be omitted.

Figure 12:
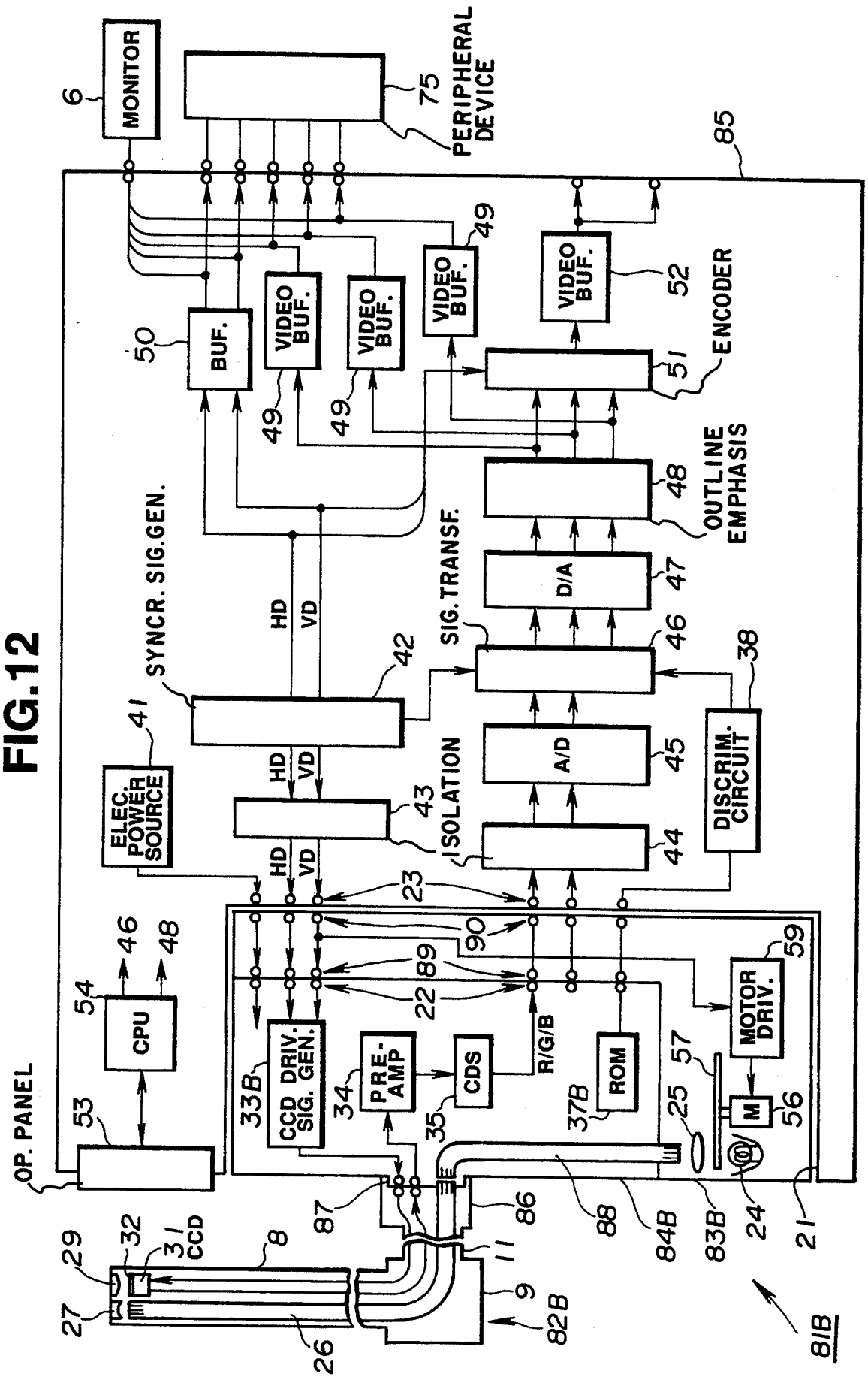

FIG. 12 shows an electronic endoscope system 81B of surface sequential type according to a third embodiment of the invention. Also in the electronic endoscope system 81B of surface sequential type, an electronic scope 82B of surface sequential type is connected to an adaptor 84B. The adaptor 84B is connected to a light-source unit 83B. Further, the light-source unit 83B is connected to a video processor body 85.

The electronic scope 82B has a connector 86 which is connected to a connector receptor 87B of the adaptor 84B. The electronic scope 82B has a light guide 26 which is connected to a light-guide connector receptor of the light source unit 83B through a light guide 88 within the adaptor 84B. The light guide 88 has an end surface thereof to which illuminating light of surface sequential type is supplied from the light-source unit 83B.

The connector 22 adjacent to a rear surface of the adaptor 83B is connected to the connector receptor 89 on a front surface of the light source unit 83B. The connector receptor 89 is conducted to a connector 90 adjacent to the rear surface through a lead wire. The connector 90 is the same in shape or configuration as the connector 22, and is connected to the connector receptor 23 of the video processor body 85. Others are the same as the aforesaid arrangements. In the present embodiment, since the connectors for light source and for signal are integrated with each other, problems relating to mounting and demounting can be reduced. Other advantages are substantially similar to those of the first embodiment.

A first modification of the third embodiment will next be described. In a case where the first modification is used in an electronic scope of surface sequential type, the first modification is arranged such that a light guide and a color filter disc are received or accommodated within an adaptor of surface sequential type, to convert white illuminating light from a light source unit of concurrent type to illuminating light of surface sequential type.

Figure 13A:
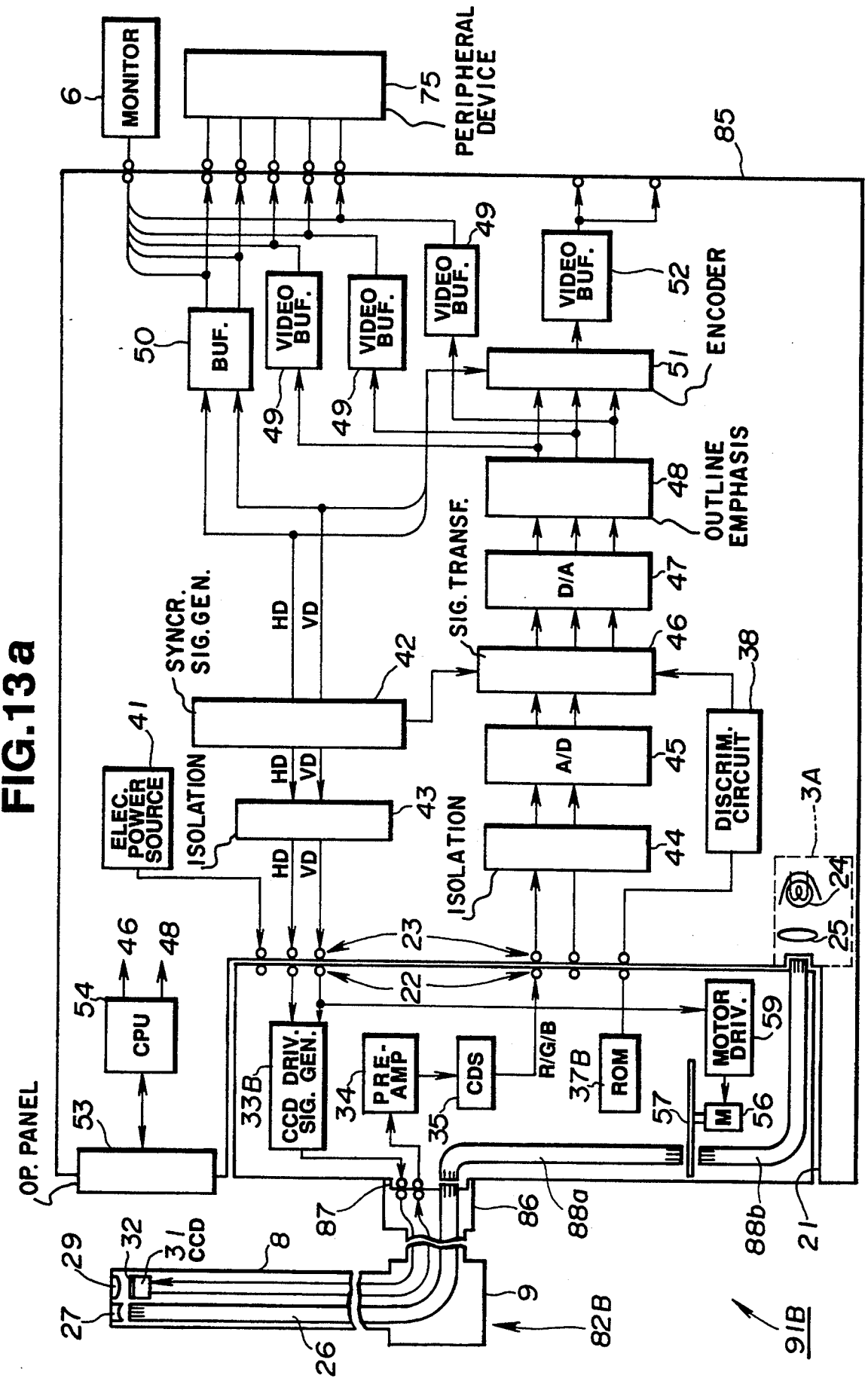
FIG. 13a is a block diagram showing an arrangement of an electronic endoscope system of surface sequential type, according to a first modification of the third embodiment of the invention.

In an electronic endoscope system 91B of surface sequential type illustrated in FIG. 13a, a portion of the light source unit 3A of concurrent type is, for example, received within a video processor body 95. A pair of light guides 88a and 88b are received within the adaptor 92B to which the electronic scope 82B of surface sequential type is connected. A color filter disc 57 rotated by a motor 56 is arranged between these light guides 88a and 88b. White illuminating light from the light source unit 3A is converted to surface-sequential illuminating light, to supply the same to the light guide 26 of the electronic scope 82B of Surface sequential type. Others are similar to the aforementioned arrangement.

In a case of the electronic endoscope system of concurrent type, a single light guide is arranged within an adaptor (not shown), white illuminating light from the light source unit 3A is transmitted, and is supplied to the light guide 26 of the electronic scope 82A of concurrent type.

According to the present modification, since it is possible to use, in common, many parts in the light source unit of surface sequential type and the light source unit of concurrent type, cost can be reduced. Also in a case where the system of surface sequential type and the system of concurrent type are exchanged with each other, problems are reduced whenever the light source unit is exchanged and demounted.

A second modification of the third embodiment of the invention will next be described with reference to FIG. 13b. The second modification is arranged such that a light guide 88 shown in FIG. 11 is provided in a light source unit 83A. Accordingly, in an electronic endoscope system 81A' of concurrent type, an electronic scope 82A of concurrent type has a connector 86 which is arranged such that a signal connector portion is connected to an adaptor 84a, and a light guide connector portion is connected to a light guide 88 which forms a light source unit 83A. Moreover, a PAL encoder 51' is used in place of an NTSC encoder 51 within a video processor body 85. Others are the same in arrangement as FIG. 11, and the adaptor 84A and the video processor body 85 are connected to each other through an electric line of the light source unit 83A.

Figure 14:
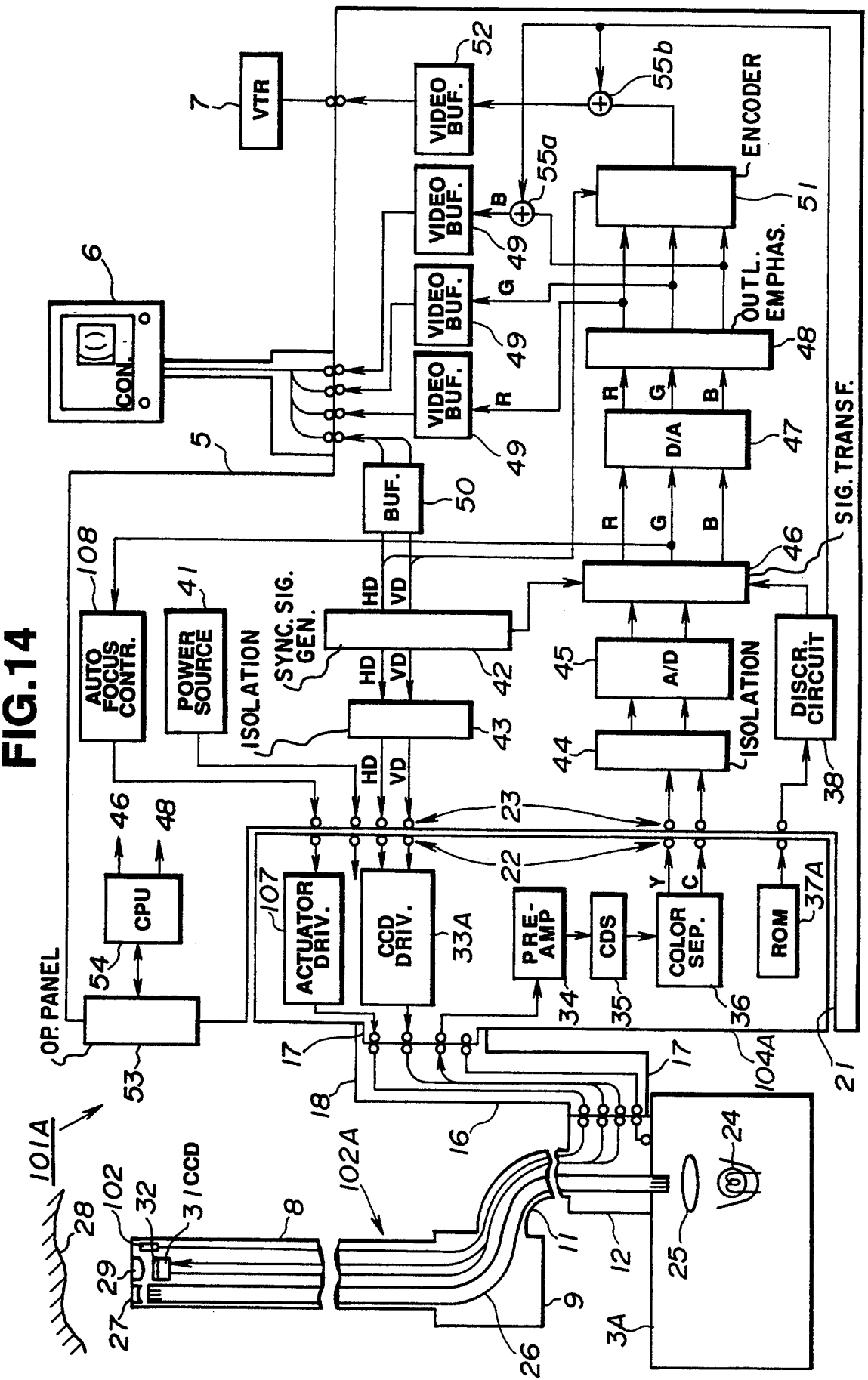

A fourth embodiment of the invention will next be described. The embodiment can be used also in an electronic scope which is provided with an autofocus function on image pickup means. In an electronic endoscope system 101A of concurrent type in the fourth embodiment illustrated in FIG. 14, in an electronic endoscope system 1A of concurrent type illustrated in FIG. 2, an actuator 102 for autofocus is received in a forward end of the electronic scope 2A of concurrent type. The electronic scope 102A of concurrent type in which an objective lens 29, for example, can be moved longitudinally or forwardly and rearwardly along an optical-axis direction is used.

An actuator drive signal is applied to the actuator 102 from the actuator drive circuit 107 within the adaptor 104A. Furthermore, the actuator drive circuit 107 is connected to an autofocus control circuit 108 within the video processor body 105 so that an objective lens 29 is moved forwardly or is moved rearwardly along the optical-axis direction, by a control signal from the autofocus control circuit 108.

Further, a G-signal of a D/A conversion circuit 47, for example, is inputted to the autofocus control circuit 108. Frequency component adjacent to a high range or area of the G-signal is extracted to perform focus detection.

FIG. 15 shows an autofocus mechanism portion. A magnet ring 111 is mounted on a third lens 29a, for example, which forms the objective lens 29. A third lens 29a and the magnet ring 111 are movable along the optical axis direction with respect to a forward-end frame 112 on which the remaining objective lens 29 is mounted.

The magnet ring 111 is biased rearwardly by a spring 113. An electromagnet 114 is fixedly mounted on the forward-end frame 112 in opposed relation to the magnet ring 111. A triangular signal is applied to the electromagnet 114 from a triangular-wave generating circuit 115 forming an actuator drive circuit 107, through an S/H circuit 116 (and a buffer, not shown).

The triangular-wave signal excites the electromagnet 114 such that a side opposed against the magnet ring 111 is brought to the same polarity, to move the magnet ring 111 forwardly by a repulsion force in accordance with a signal value. The triangular-wave generating circuit 115 outputs a triangular-wave signal, when an enable signal is applied to the triangular-wave generating circuit 115 from a CPU 117 which forms the autofocus control circuit 108.

The autofocus control circuit 108 takes into or fetches the G-signal under a condition that the third lens 29a is moved, and extracts a signal component adjacent to a high range or area through an HPF 118. The autofocus control circuit 108 detects frequency distribution by an FFT 119, detects peak frequency which becomes peak of the frequency distribution, by a peak frequency detecting circuit 10 and transmits the peak frequency to the CPU 117. The CPU 117 compares the peak frequency in a case where the peak frequency is detected before and after in time. In a case of the maximum peak frequency, that is, in a case where spatial frequency is brought to a highest focus condition, a hold signal is outputted to an S/H circuit 116 to maintain the objective lens 29 under a focus condition.

Other arrangements are the same as those of the system 1A illustrated in FIG. 2. In FIG. 15, the electronic scope 102A of concurrent type provided with the actuator 102 for autofocus is connected, but the system 1a can be used also in the electronic scope 2A of concurrent type illustrated in FIG. 2. In a case where the electronic scope 2A of concurrent type is used, function is brought to the function the same as that of the first embodiment.

In a case of the surface successive type, the autofocus mechanism is similar to that described above, and the description thereof will be omitted.

Figure 16B:
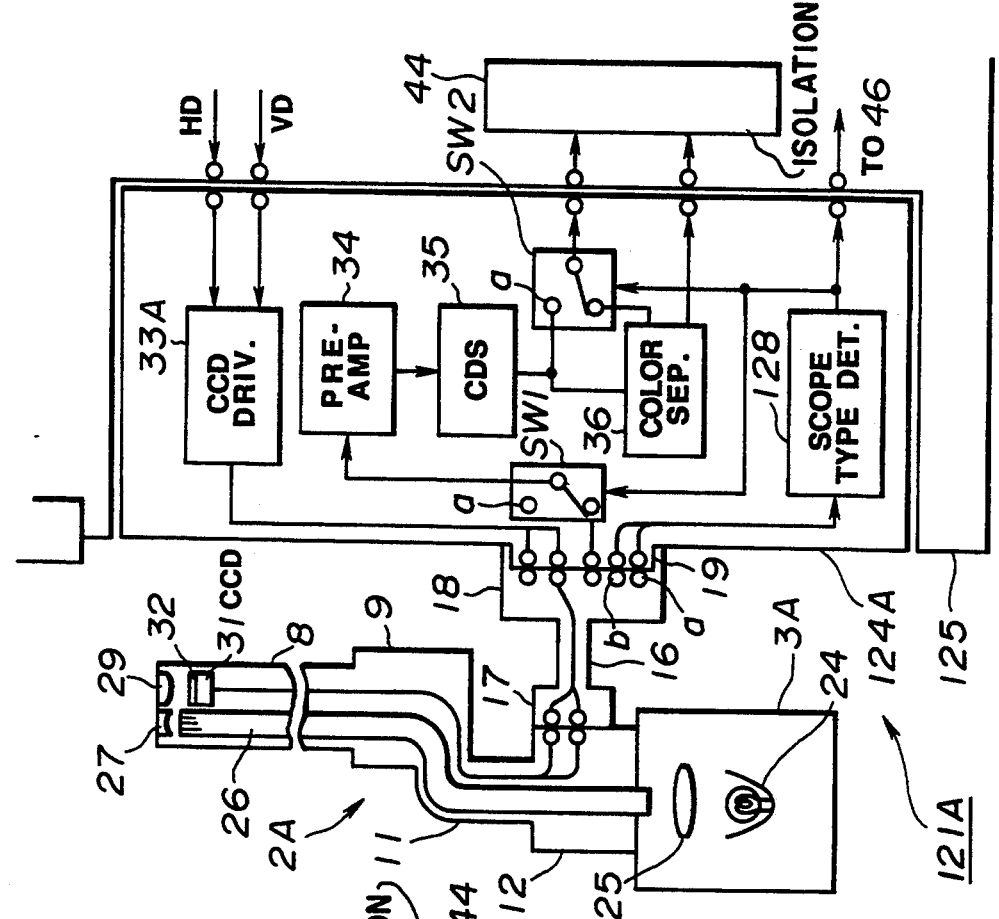
FIGS. 16 and 17 relate to a fifth embodiment of the invention, FIGS. 16a and 16b being arrangement views respectively showing principal portions of electronic endoscope systems for infrared and for concurrent type according to the fifth embodiment.
Figure 16A:
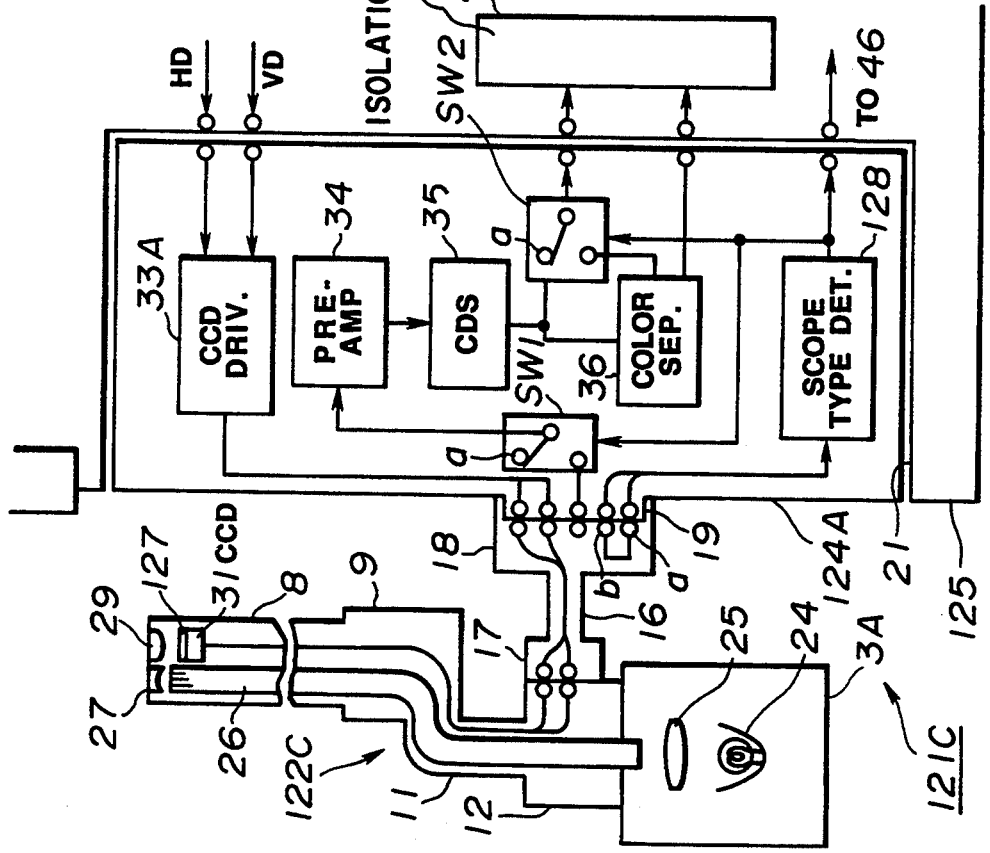

A fifth embodiment of the invention will be described with reference to FIG. 16. The embodiment is so arranged as to be capable of being used also in an electronic scope which obtains an infrared image, for example, as an endoscope image due to special or specific light other than a visible range or area. In the fifth embodiment, an electronic endoscope system 121C in a case where the infrared electronic scope 122C is connected, is brought to one illustrated in FIG. 16(a). The electronic endoscope system 121A, in a case where the electronic scope 2A of concurrent type is connected, is brought to one illustrated in FIG. 16(b). Also, in a case of any of the electronic scope 122C or 2A, the light source unit 3A and the adaptor 124A are common (of course, the video processor body 125 is also common).

The infrared electronic scope 122C is arranged such that, in the electronic scope 2A of concurrent type, an infrared transparent filter 127 is mounted on the CCD 31 in place of the simple-plate color tip 32. Accordingly, an image of an infrared area is imaged on an image pickup surface of the CCD 31. Furthermore, in the electronic scope 2A of concurrent type and the infrared electronic scope 122C, pins a and b for discrimination are provided on a portion of a connector 18. For example, in the electronic scope 2A of concurrent type, the pins a and b are released, while in the infrared electronic scope 122c, the pins a and b are short-circuited.

A scope-type detecting circuit 128 is arranged within the adaptor 124A, for controlling switching of switches SW1 and SW2 of the adaptor 124A in accordance with type of the detected scope. The scope-type detecting circuit 128 outputs a control signal to a signal conversion circuit 46 within a video processor body 125, to perform signal processing suited to or adapted for respective signals.

For example, in a case where the infrared electronic scope 122C is connected, the switches SW1 and SW2 are such that the side of the contact a is conducted. Similarly to a case where the electronic scope 2B of surface sequential type is connected in FIG. 10, a signal of a single system is outputted toward the video processor body 125. However, differentiated from a case of the surface sequential type in which three signals are successively outputted in a time-series manner, a single signal is successively outputted. In a case of the video processor body 125, in the signal conversion circuit 46, writing is performed simultaneously to the three memories 46-1, 46-2 and 46-3, for example, and display is performed by white and black on the monitor 6 (the arrangement may be such that only one memory is used to perform display by a simple color).

Figure 17:
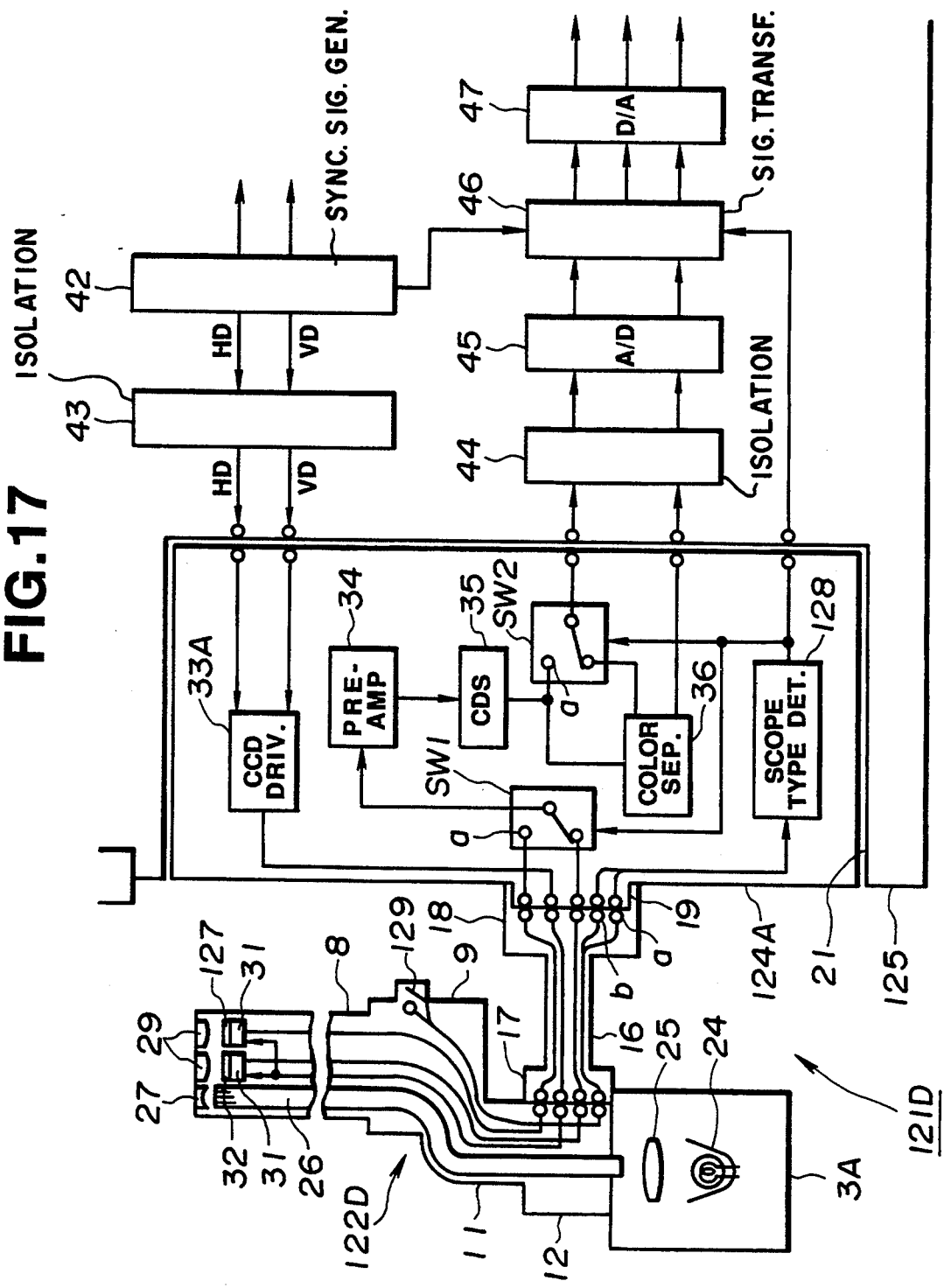

Further, the present embodiment can be used for the infrared electronic scope 122D of concurrent type which is provided with an infrared image pickup element on the electronic scope of concurrent type as shown in FIG. 17. In this case, the electronic scope 122D is provided with a selection switch 129. The selection switch 129 is turned ON or OFF, whereby the pins a and b can be set to a conductive condition or a released condition. Signal processing of the adaptor 124A and the video processor body 125 can selectively be set.

In connection with the above, the arrangement may be such that a memory is further provided on a signal conversion circuit 46, one of images different in a single frame period of time from each other can be superimposed upon the other image and can be displayed. If the electronic scope 122D illustrated in FIG. 17 is used, it is possible to selectively display a visible image and an infrared image without exchange of the electronic scope 122D and the like.

In the surface-sequential image pickup system, light is dissolved into lights having wavelength ranges or areas of R, G and B that are generally three primary colors in a visible area, and is successively irradiated. However, irradiation is performed reaching an area of ultraviolet rays and infrared rays as those for medical treatment or a special or specific use, whereby there is a case where information out of the visible area of eyes of a human being is obtained. By infrared observation due to the infrared rays, that is, by measurement of heat distribution and, particularly, by the fact that distribution of oxygen concentration within blood and a quantity of hemoglobin is measured for medical treatment use, it is possible to observe a lesion or the like at a lower-layer level under conjunctive.

Accordingly, in a case of such measurement, it is required in the prior art that switching is made from R, G and B sequential lights to infrared, R, G and G lights or infrared, R, G and B sequential lights. To the contrary, if the present embodiment is used, a normal endoscope image within a visible area and a normal infrared endoscope image can be produced as a white light source 3A for a wide use as it is and without exchange of the adaptor 124A. The present fifth embodiment is an embodiment which produces an infrared image. However, an ultraviolet transparent filter is mounted on the CCD, whereby an ultraviolet image can also be produced similarly.

Further, the present embodiment can also be applied to a system of surface sequential type.

Figure 18:
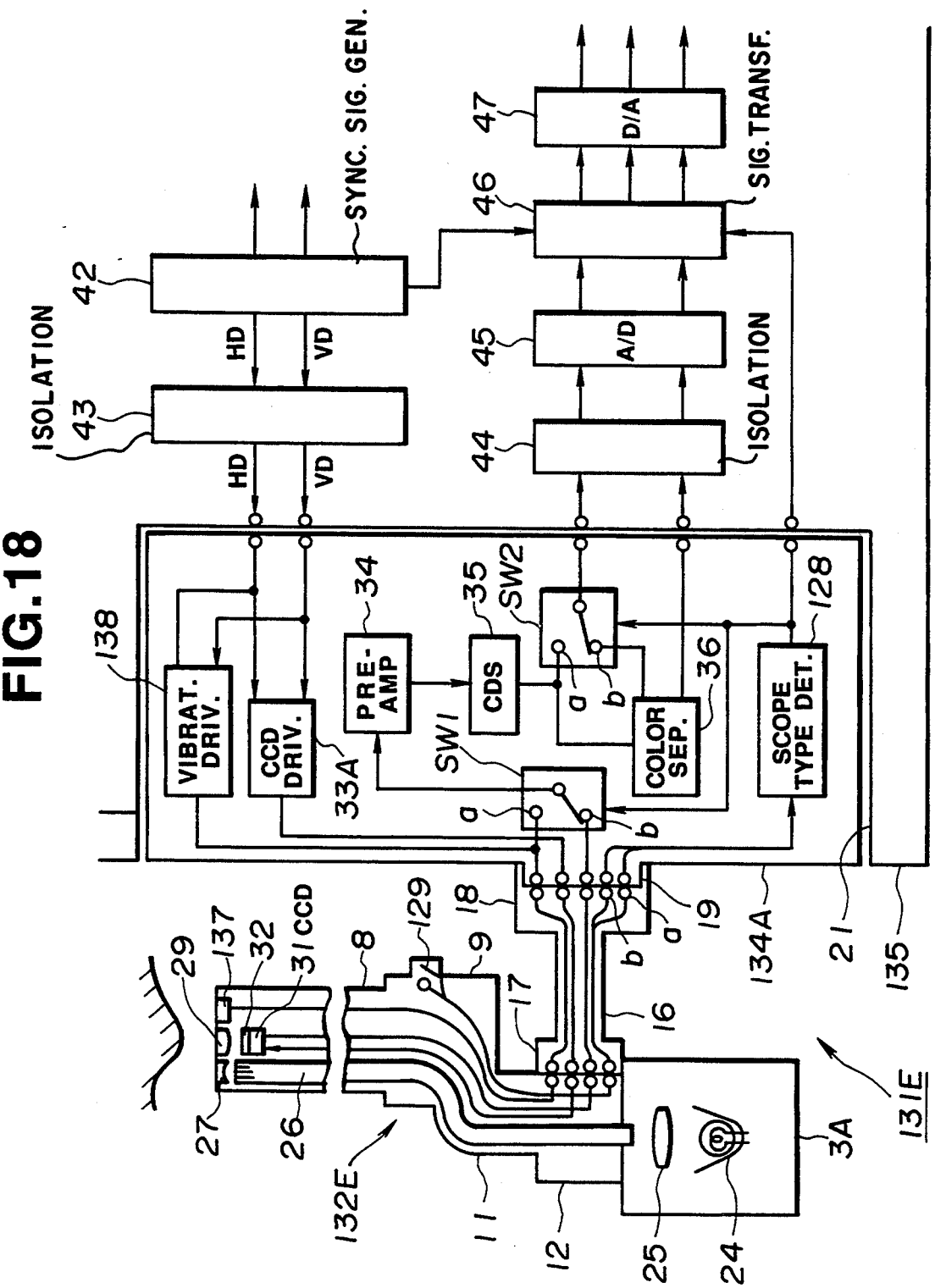
FIG. 18 is an arrangement view showing a principal portion of an ultrasonic electronic endoscope system according to a sixth embodiment of the invention.

A sixth embodiment of the invention will next be described. The embodiment is arranged such that an ultrasonic image can also be produced. An ultrasonic electronic endoscope system 131E illustrated in FIG. 18 comprises an ultrasonic electronic scope 132E which is provided with an ultrasonic vibrator (or piezoelectric transducer) 137 at a forward end of an electronic scope of simultaneous or concurrent type, for example. The ultrasonic electronic scope 132E is of structure in which, in scope 122D illustrated in FIG. 17, an ultrasonic vibrator 137 is provided in place of a CCD 31 and an infrared transparent filter 127.

The ultrasonic vibrator 137 comprises a vibrator array in which a minute vibrator, for example, is arranged in a two-dimensional manner, and a selective circuit (not shown) for selecting a driving vibrator. The ultrasonic vibrator 137 is of structure that, when a vibrator drive signal is applied, the selective circuit successively selects the vibrator in a horizontal direction and in a vertical direction to apply the drive signal.

The ultrasonic electronic scope 132E is connected to the video processor body 135 through an adaptor 134A. The adaptor 134A is provided with an ultrasonic-vibrator drive circuit 138 for driving the ultrasonic vibrator 137, in addition to function of the adaptor 124 shown in FIG. 17.

Synchronous signals HD and VD from a synchronous-signal generating circuit 42 of a video processor body 135 are applied to the ultrasonic-vibrator drive circuit 138 through an isolation circuit 43, similarly to the CCD drive-signal generating circuit 33A.

Further, an ultrasonic echo signal received by the ultrasonic vibrator 137 is inputted to the preamplifier 34 through a contact a of a switch SW1. Similarly to a case illustrated in FIG. 17, when the switch 129 is turned OFF, two switches SW1 and SW2 are such that a contact b is selected, and a condition is brought to a condition of a signal processing system with respect to an electronic scope of concurrent type.

On the other hand, when the switch 129 is turned ON, the two switches SW1 and SW2 are such that the contact a is selected, bringing forth a condition of a signal processing system with respect to an ultrasonic scope. Under this condition, processing similar to an infrared image is performed. In the present embodiment, a video processor body 135 the same in arrangement as the video processor body 125 in a case illustrated in FIG. 17 can be used. Others are the same as those illustrated in FIG. 17.

In the present embodiment, in a case where an affected or diseased part or the like is inspected with endoscope as, for example, an electronic scope of concurrent type, and more detailed information is desired with respect to the affected part, a forward end is in contact with a side of the affected part to turn ON the switch 129, whereby an ultrasonic wave is enumerated with respect to the side of the affected part. Echo from a portion varied in acoustic impedance at the side of the affected part is received by the ultrasonic vibrator 137, and is to an electric signal so as to be brought to an echo signal. Signal processing similar to a case of the infrared CCD is performed, and an ultrasonic image is displayed on the monitor 6.

According to the present embodiment, since there can be produced acoustic image information in addition to optical image information, it is possible to provide inspecting means more suitable for performing diagnosis.

Figure 19:
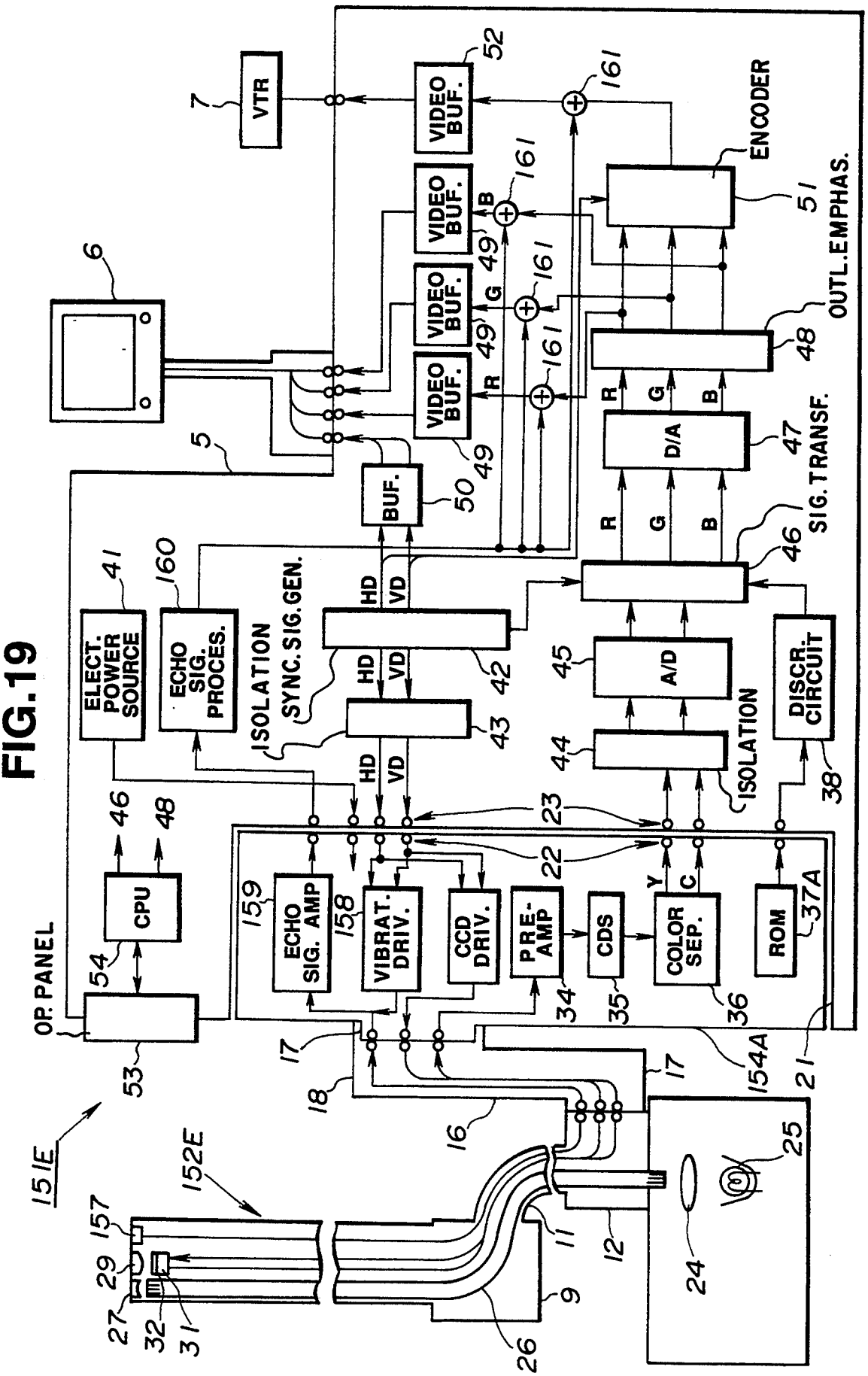
FIG. 19 is an arrangement view showing an ultrasonic electronic endoscope system according to a modification of the sixth embodiment of the invention.

In connection with the above, the arrangement may be such that an ultrasonic image can be displayed together with an endoscope image, similarly to the modification of the sixth embodiment, illustrated in FIG. 19.

An ultrasonic electronic endoscope system 151E illustrated in FIG. 19 comprises an ultrasonic electronic scope 152E which is provided with an ultrasonic vibrator 157 at a forward end of an electronic scope of concurrent type, for example.

The ultrasonic electronic scope 152E is connected to a video processor body 155 through an adaptor 154A. An ultrasonic-vibrator drive circuit 158 for driving the vibrator 157 and an echo-signal amplifier circuit 159 for amplifying the ultrasonic echo signal received by the ultrasonic vibrator 157 are received or accommodated within the adaptor 154A, in addition to function of the adaptor 4A shown in FIG. 2.

The synchronous signals HD and VD from the synchronous-signal generator 42 of the video processor body 155 are applied to the ultrasonic-vibrator drive circuit 158 through an isolation circuit 43, similarly to the CCD drive-signal generating circuit 33A.

Moreover, the ultrasonic echo signal amplified by the echo-signal amplifier circuit 159 is inputted to the echo-signal processing circuit 160 within the video processor body 155 and is brought to an image signal. Subsequently, the ultrasonic echo signal is added to an output signal from an outline emphasizing circuit 48 and the like by an adder 161 so that an ultrasonic image can be displayed on the monitor 6. Others are substantially the same in arrangement as the system illustrated in FIG. 2.

Figure 20:
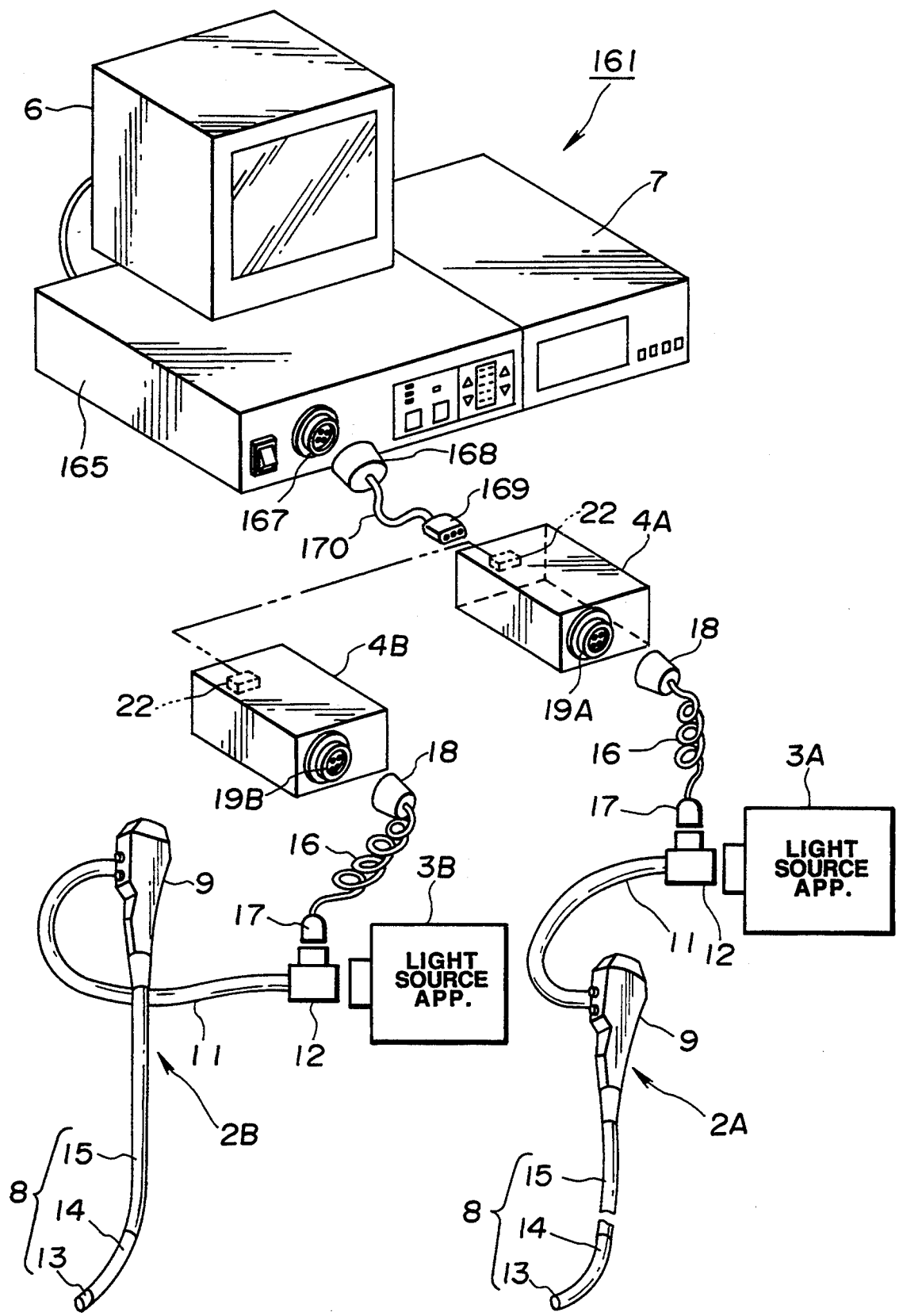
FIG. 20 is an entire arrangement view showing an electronic endoscope system according to a seventh embodiment of the invention.

FIG. 20 shows an electronic endoscope system 161 according to a seventh embodiment of the invention. The embodiment is arranged such that an adaptor is not directly connected to a video processor body, but the adaptor is connected to the video processor body through a cable.

In a system 1 illustrated in FIG. 1, the video processor body 5 is provided with a recess 21 which is capable of receiving an adaptor 4A or 4B. However, the electronic endoscope system 161 is arranged such that a connector receptor 167 provided at a front surface of the video processor body 165 and a connector 22 adjacent to a rear surface of the adaptor 4A or 4B are connected to each other through a cable 170 having both ends thereof provided with connectors 168 and 169. Others are the same as those of the first embodiment.

Figure 21:
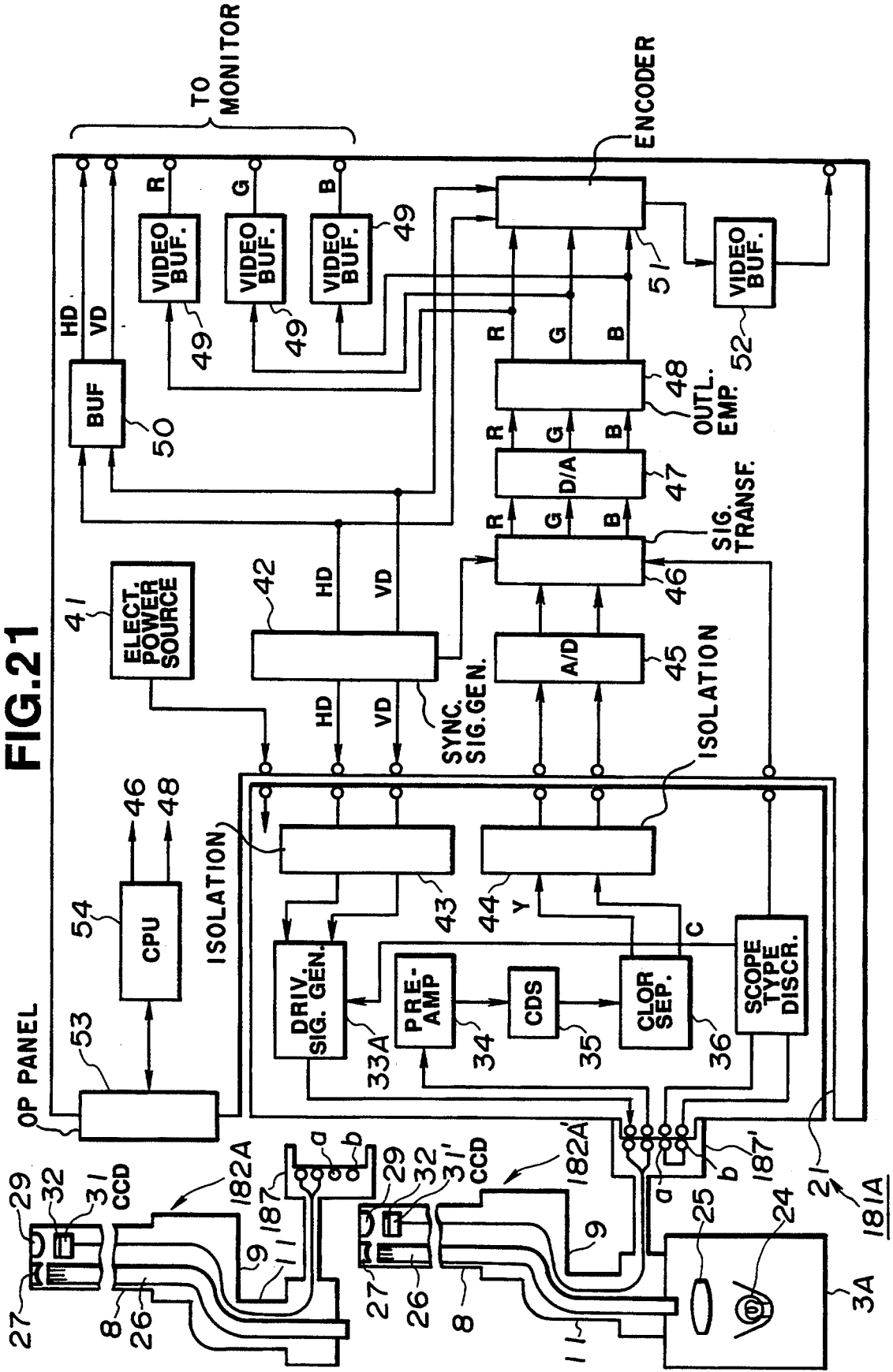
FIGS. 21 and 22 relate to an eighth embodiment of the invention, FIG. 21 being an arrangement view showing an electronic endoscope system of concurrent type according to the eighth embodiment of the invention.

FIG. 21 shows an electronic endoscope system 181A of concurrent type according to an eighth embodiment of the invention. The embodiment copes with or deals with image pickup means of the number of different picture elements.

Furthermore, an isolation circuit is provided not adjacent to a video processor body, but adjacent to an adaptor.

Electronic scopes 182A and 182A' of concurrent type comprise CCDs 31 and 31' differing from each other in the number of picture elements. Discrimination-signal generating means indicating that the scopes differ in the number of picture elements is provided on signal connectors 187 and 187' of the respective electronic scopes 182 and 182'. In the present embodiment, the CCD 31' for example, has a number of picture elements four times the CCD 31 (the picture elements twice in a vertical direction, and the picture elements twice in the horizontal direction, for example). The discrimination-signal generating means is so arranged as to be capable of performing discrimination by an arrangement in which pins a and b are released and an arrangement in which pins a and b are short-circuited, for example.

The adaptor 184A is provided with a scope type discriminating circuit 188 which judges whether the pins a and b are released or short-circuited, to thereby judge (detect) which electronic scope 182I (I=A or A') is. The detected signal is outputted to a side of the video processor body 185, and is applied to a control terminal for vertical and horizontal transmission signals of the drive-signal generating circuit 33A.

The drive-signal generating circuit 33A outputs vertical and horizontal transmission signals which reads out the number of four-time picture elements in a case of the CCD 31', by a level of "H" or "L" of the output signal from the scope type discriminating circuit 188. Specifically, vertical and horizontal transmission signals $\phi$V and $\phi$H illustrated in FIG. 6e are, in a case of the CCD 31', outputted during four-time period of time.

Moreover, in the signal conversion circuit 46, image data reading-out four times a case of the CCD 31 (twice in the vertical direction, and twice in the horizontal direction) is performed in a case of the CCD 31', in accordance with an output signal from the scope type judging circuit 188.

Figure 22:
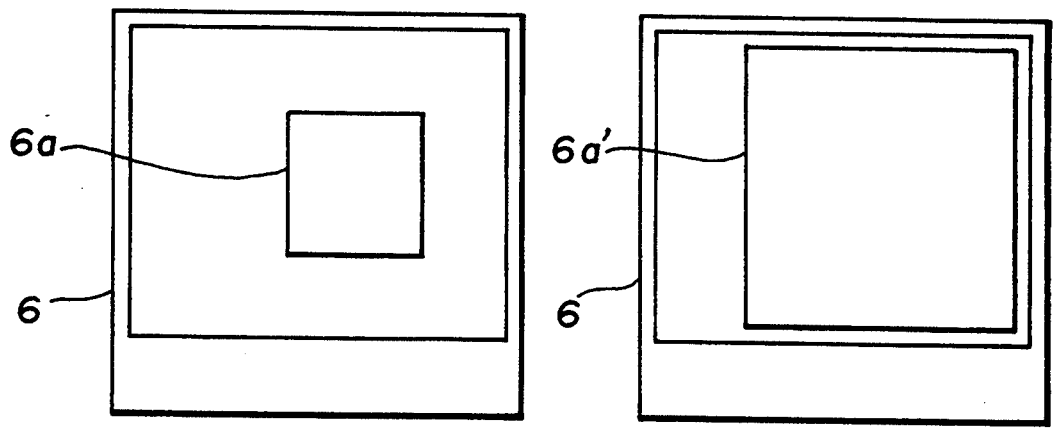

Accordingly, display is performed on the monitor 6 by an image area 6a' four-times an image area 6a in a case of the CCD 31, in a case of the CCD 31' as shown in FIG. 22.

Furthermore, in the present embodiment, the isolation circuits 43 and 44 are arranged not within the video processor body 185, but within the adaptor 184A. In this case, in a case where the adaptor 184A is connected to the video processor body 185, it is possible to conduct a casing chassis of the adaptor 184A with a secondary circuit casing chassis within the video processor body 185. In this connection, in this case, GND terminals (which are brought respectively to GND terminals of a patient circuit) of various circuits within the adaptor 184A are floated from the casing chassis of the adaptor 184A.

In a case where the isolation circuits 43 and 44 are provided on the video processor body 185, since the casing chassis adjacent to the adaptor 184A is conducted to the GND of the patient circuit, the casing chassis is required to be isolated or insulated from the casing chassis adjacent to the video processor body 185.

Although the present embodiment has been described with reference to the concurrent type, the present embodiment can be applied also to the surface sequential type.

Further, for simplification, in the present embodiment, the one number of picture elements are four (4) times the other number of picture elements. However, the present embodiment may cope also with a case of other multiples such as that an interpolation circuit, or an image magnification or enlargement circuit or an image reduction circuit is provided on the signal conversion circuit 46, or the like.

Figure 23:
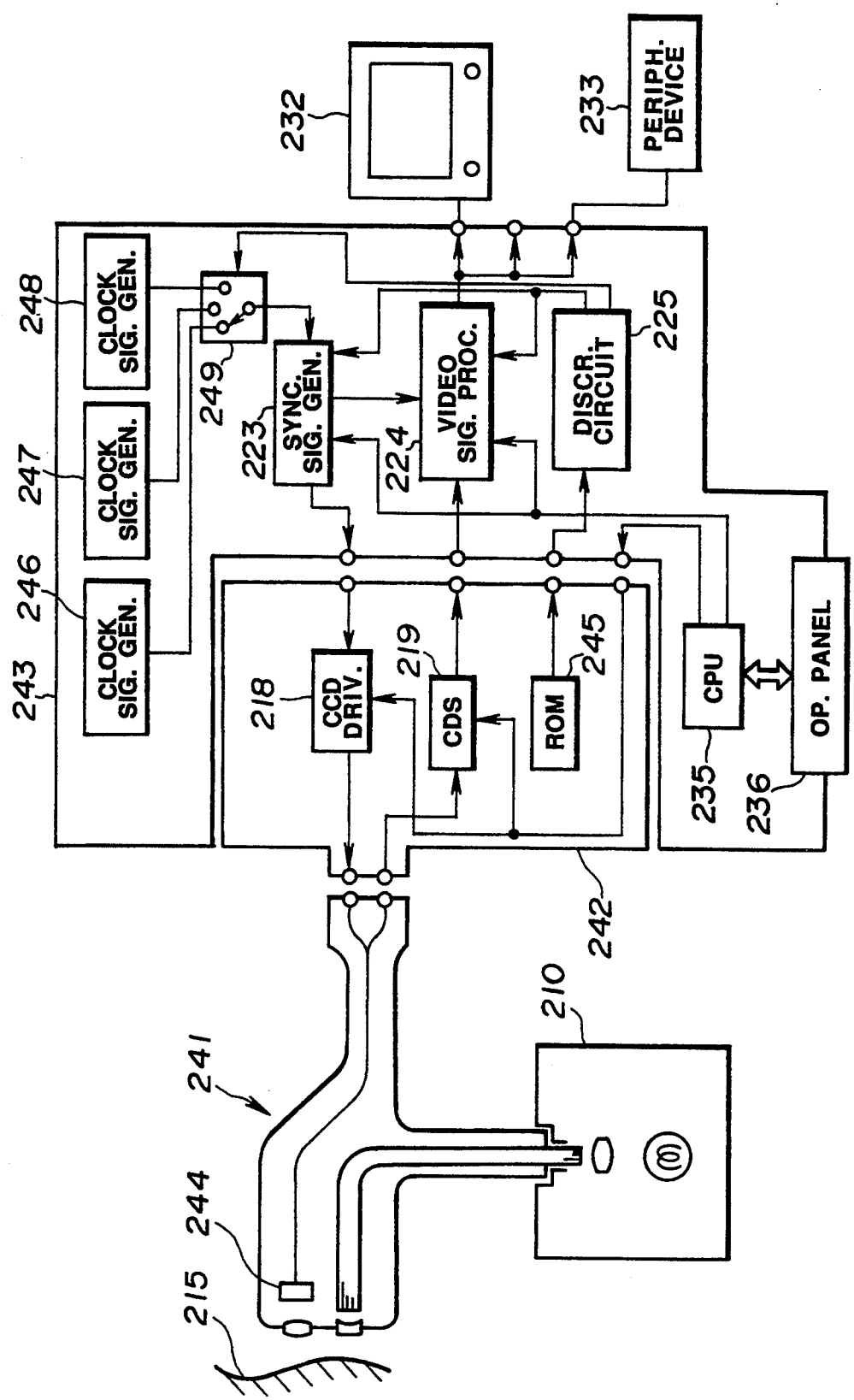
FIG. 23 is an entire arrangement view showing an electronic endoscope system of concurrent type.

Moreover, the arrangement may be brought to one illustrated in FIG. 23 so as to arrange an electronic endoscope system capable of coping with the different number of picture elements.

The present system shows an arrangement in a case where the number of picture elements of the CCD 244 which is provided on the electronic scope 241 differs.

In the present system, scope corresponding units 242 are prepared for 30,000 picture elements, 100,000 picture elements and 200,000 picture elements, for example. A suitable or adapted scope corresponding unit 242 is connected to the processor body 243 in accordance with the number of picture elements of the CCD 244 within the electronic scope 241.

The scope corresponding unit 242 is provided with a ROM 245 for generating characteristic information such as picture-element information indicating the number of picture elements of the CCD with which the unit copes, and the like. The type or kind and characteristic of the scope corresponding unit 242, that is, the number of picture elements of the CCD 244 within the electronic scope 241 are judged by the judging circuit 25 of the processor body 243.

The processor body 243 is provided with three clock-signal generators 246, 247 and 248 for generating clock signals so as to cope with the number of picture elements of the CCD. The clock signals generated by these generators are supplied to the synchronous-signal generating circuit 23 through the switch circuit 249. The three (3) clock-signal generators 246, 247 and 248 are provided for 30,000 picture elements, 100,000 picture elements and 200,000 picture elements, for example. Selection of the clock signals by the switch circuit 249 is switched by a selective signal on the basis of the judgment results of the judging circuit 25.

Generally, under the same image appearing size condition in which image plane sizes of the output image signals are the same as each other, if the number of picture elements of the CCD 244 differs, it is required to switch drive frequency of the CCD 244 in accordance therewith. In the present embodiment, the clock signals different from each other from the three (3) clock signal generators 246, 247 and 248 are selected whereby the drive frequency of the CCD drive signal is switched.

If the scope corresponding unit 242 is connected to the processor body 243, the number of picture elements of the CCD 244 is judged by the judging circuit 25 on the basis of the characteristic information from the ROM 245. In accordance with the judgment results, an input to the switch circuit 249 is switched, and the clock signal generator corresponding to the number of picture elements of the CCD is selected by the three (3) clock signal generators 246, 247 and 248. The clock signal outputted from the selected generator is inputted to the synchronous-signal generating circuit 223 so that a horizontal transmitting drive signal and a vertical transmitting drive signal with respect to the CCD 244 are generated with the clock signals serving as a source signal.

The synchronous signals such as the horizontal transmitting drive signal, the vertical transmitting drive signal and the like are inputted to the CCD drive circuit 218. The CCD 244 is adequately driven by the CCD drive signal having a drive frequency which is suited for the number of picture elements outputted from the CCD drive circuit 218.

Furthermore, a control signal is also inputted to the image signal processing circuit 224 on the basis of the judgment results of the judging circuit 225 so that operation mode is switched. Thus, a photoelectric transfer output of the CCD 244 is adequately processed in image signal and is sent to the TV monitor 232 and the peripheral instrument 233.

In this manner, the scope corresponding unit suited for the number of picture elements of the CCD is connected to the processor body, and the clock-signal generator is selected in accordance with the unit, to switch the drive frequency of the CCD drive signal, whereby it is possible to cope with a plurality of kinds or types of electronic scopes provided with CCDs different in the number of picture elements by minimum switching of circuit. Thus, reduction in cost of the apparatus and miniaturization are made possible.

Figure 24:
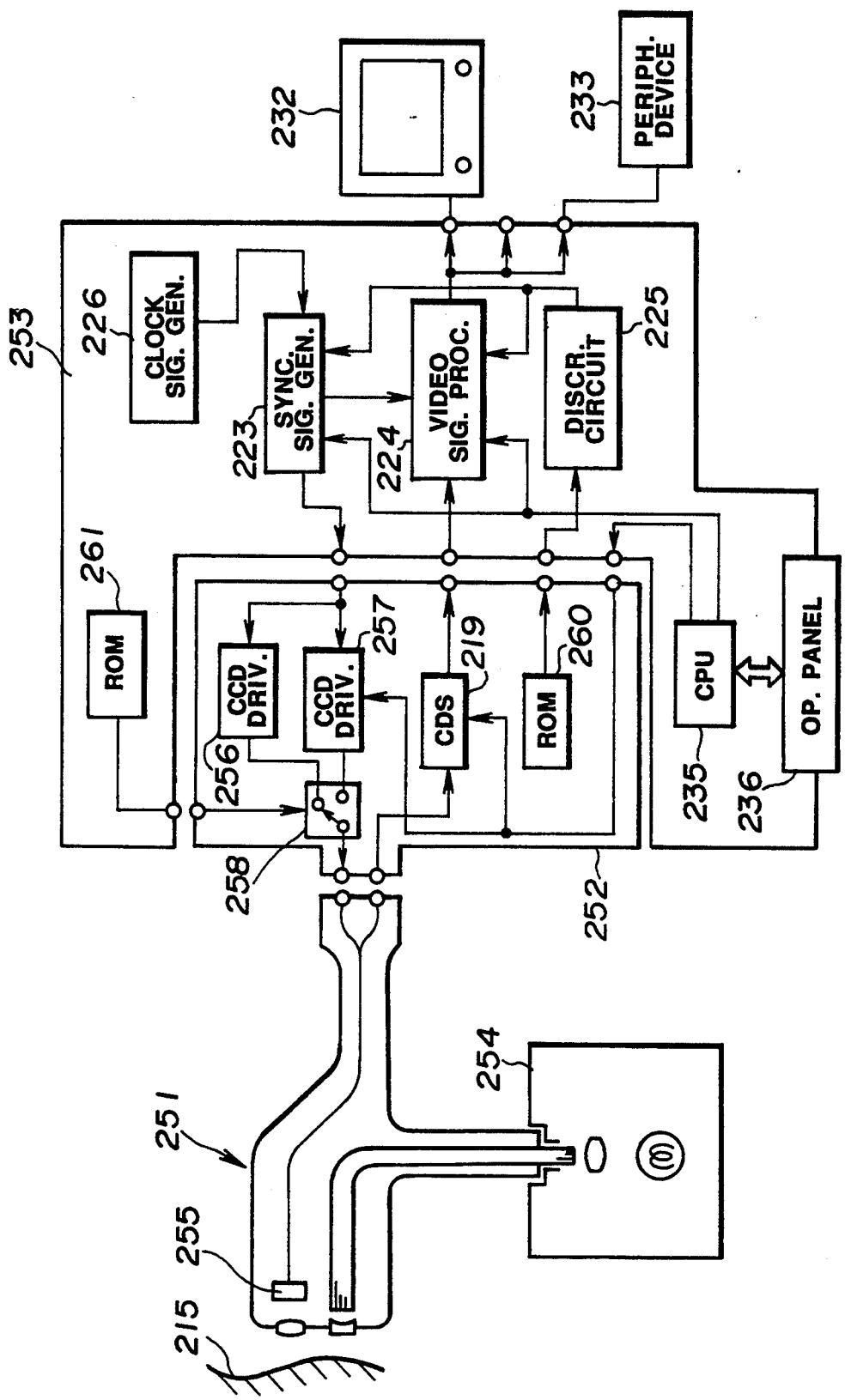
FIG. 24 is an entire arrangement view showing an electronic endoscope system of concurrent type according to a modification of the arrangement illustrated in FIG. 23.

FIG. 24 shows an arrangement of an electronic endoscope system which can cope with two image pickup systems including a concurrent type and a surface sequential type.

The concurrent type and the surface sequential type have advantages or disadvantages, and are used properly by the field of parts of the observation object. The system is provided with two CCD drive circuits 256 and 257 for a concurrent type and for a surface sequential type, on the scope corresponding unit 252 so that the system can cope with a plurality of image pickup systems.

The present embodiment can cope with two image pickup systems including the concurrent type and the surface sequential type, with respect to the specific CCDs, that is, the CCDs the same in number of picture elements as each other. Accordingly, in accordance with the number of picture elements of the CCD 255 within the electronic scope 251, a suitable scope corresponding unit 252 is connected to the processor body 253. Moreover, a light-source unit 254 corresponding to the image pickup system is connected to the electronic scope 251.

The scope corresponding unit 252 is provided with a CCD drive circuit 256 for surface sequential type and a CCD drive circuit 257 for concurrent type. Outputs from the representative two drive circuits are inputted to the switch circuit 258. By the switch circuit 258, the CCD drive signal corresponding to the image pickup system is selected. Further, a ROM 260 is provided for generating characteristic information had by the scope corresponding unit 252. Kind or type of the scope corresponding unit 252 is judged by the judging circuit 25 of the processor body 253.

The processor body 253 is provided with a ROM 261 in which the characteristic information for judging whether the processor body 253 is for the concurrent type or for the surface sequential type is stored. The characteristic information is inputted to the switch circuit 258 within the scope corresponding unit 252 so that an output from the CCD drive circuit suited for the image pickup system is selected. If the scope corresponding unit 252 is connected to the processor body 253, the number of picture elements of the CCD 255 is judged by the judging circuit 225 on the basis of the characteristic information from the ROM 260. In accordance with the judgment results, operation modes of the synchronous-signal generating circuit 223, the image-signal processing circuit 224 and the like are switched. Furthermore, the input to the switch circuit 258 is switched so as to be suited for the image pickup system of the processor body 253 on the basis of the characteristic information from the ROM 261 of the processor body 253, and the CCD drive signal from the CCD drive circuit 256 or 257 is selected. At this time, the synchronous signal is inputted to the CCD drive circuits 256 and 257 from the synchronous-signal generating circuit 223. Thus, the CCD drive signals corresponding respectively to the image pickup systems are generated. The selected CCD drive signal is supplied to the CCD 255 of the electronic scope 251 so that the CCD 255 is driven under an optimal condition. That is, the scope corresponding unit 252 is such that an output from a circuit is selected so as to become optimum in a combination with the processor body 253.

Further, a photoelectric transfer output from the CCD 255 is inputted to the image-signal processing circuit 224 through the CDS circuit 219. The photoelectric transfer output from the CCD 255 is processed in its image signal here and is sent to the TV monitor 232 and the peripheral instrument 233.

If an attempt is made to cause the processor body to have functions corresponding to the concurrent type and the surface sequential type, there are problems that the signal processing circuit increases in size or becomes bulky, the cost increases, and the like. However, like the present embodiment, the processor body 253 and the scope corresponding unit 252 are brought to separate detachable arrangements, and the CCD drive signal outputted from the scope corresponding unit 252 is selected in accordance with the image pickup system, whereby it is possible to cope with a plurality of image pickup systems by minimum switching of the circuit.

Figure 25:
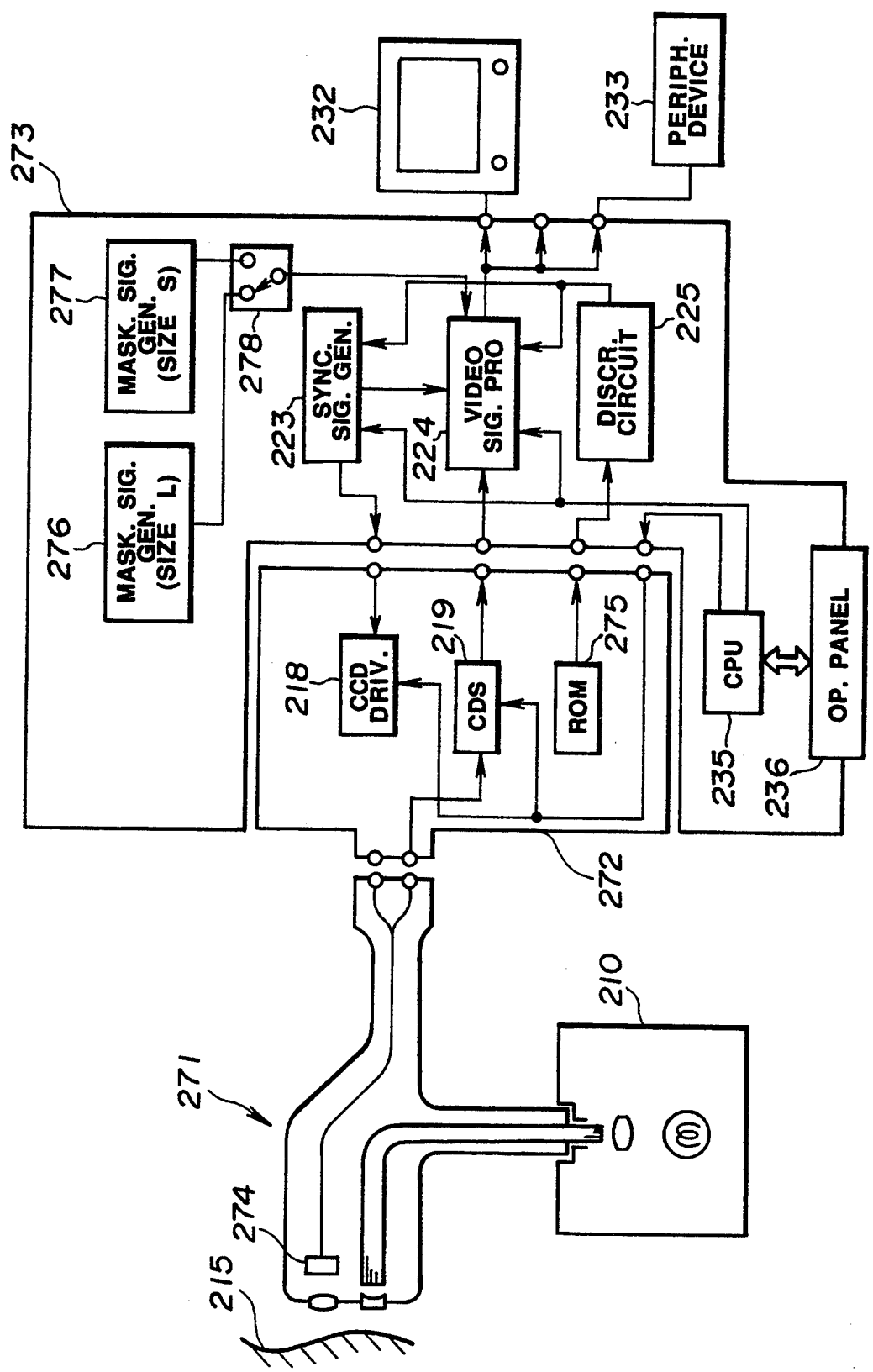
FIG. 25 is an entire arrangement view showing an electronic endoscope system of concurrent type.

FIG. 25 shows a system for altering or changing a display area in accordance with the number of picture elements of the CCD of the electronic scope.

The arrangement is such that a suitable scope corresponding unit 272 is connected to the processor body 273 in accordance with the number of picture elements of the CCD 274 within the electronic scope 271.

The scope corresponding unit 272 is provided with a ROM 275 for generating characteristic information such as picture element information and the like indicating the number of picture elements of the CCD to which the unit corresponds. The arrangement is such that the kind or type and characteristic of the scope corresponding unit 272, that is, the number of picture elements of the CCD 274 within the electronic scope 271 is judged by the judging circuit 25 of the processor body 273.

The processor body 273 is provided with mask-signal generators 276 and 277 for setting the size of the screen or image plane of an output image signal in accordance with the number of picture elements of the CCD. The mask-signal is a signal for deleting (masking) a signal equivalent to a peripheral edge of an appearing image plane to set an image appearing area. The mask-signal generator 276 outputs the mask signal for an appearing image plane of large size, while the mask-signal generator 277 outputs the mask signal for an appearing image plane of small size.

The mask signals generated by the mask-signal generators 276 and 277 are supplied to the image-signal processing circuit 24 through the switch circuit 278. Selection of the mask signal by the switch circuit 278 is switched by a selective signal on the basis of the judgment results of the judging circuit 25. Here, when, for example, the number of picture elements of the CCD is 30,000 picture elements, a mask signal for an appearing image plane of small size is selected, while, when the number of picture elements is 200,000 picture elements, a mask signal for a large appearing image plane is selected.

Generally, in the electronic endoscope apparatus, the image appearing area on the TV monitor is changed in accordance with the number of picture elements of the image pickup element. That is, in a case where the number of picture elements of the image pickup element is less or is reduced, if the image appears on the entire image plane of the monitor, the image is deteriorated or degraded. Accordingly, in a case where the picture elements of the CCD is few 30,000 picture elements, for example, the image appearing area is brought to about ¼ with respect to the image appearing area in a case of 200,000 picture elements.

When the scope corresponding unit 272 is connected to the processor body 273, the number of picture elements of the CCD 274 is judged by the judging circuit 25, on the basis of the characteristic information from the ROM 275. Depending upon the judgment results, an input to the switch circuit 278 is switched, and an output from one of the mask-signal generators 276 and 277 corresponding to the number of picture elements of the CCD is selected by the mask-signal generator. The mask signal outputted from the selected generator is inputted to the image-single processing circuit 224. The size or dimension of the appearing image plane onto the TV monitor 32 is determined or decided in accordance with the mask signal.

The image-signal processing circuit 224 is provided with a video mixer circuit so that an unnecessary or unrequired signal area of the peripheral edge of the appearing image plane in the image signal is deleted by the gate means on the basis of the mask signal. That is, the image signal and the mask signal are mixed with each other upon image-signal processing, whereby an un-required signal area of the image signal is deleted. Thus, the image appearing area of the image signal at the TV monitor 232, outputted in accordance with the number of picture elements of the CCD is changed.

In connection with the above, at this time, a control signal is inputted also to the image-signal processing circuit 224 and the like on the basis of the judgment results of the judging circuit 225 so that the operation mode is changed. The photoelectric transfer output from the CCD 274 is processed in image signal in an optimum manner.

Figure 26A:
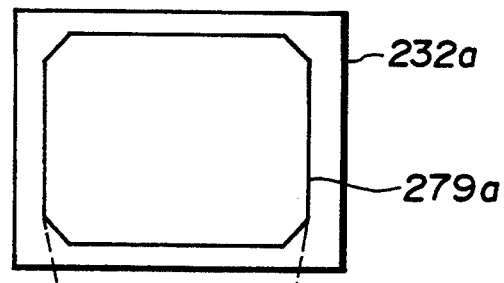
FIG. 26 is a view for explanation showing an appearing image plane of a TV monitor.
Figure 26B:
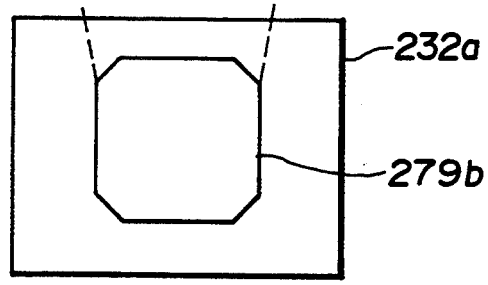

As shown in FIG. 26, in the TV monitor 232, a subject image is displayed on the display image plane or picture plane 232a by the monitor. However, the appearing image plane 279a having a large image appearing area is displayed as shown in FIG. 26a by the aforesaid masking processing when the number of picture elements of the CCD 274 is 200,000 picture elements, while, when the number of picture elements is 30,000 picture elements, the appearing image plane 279b having a reduced image appearing area is displayed as shown in FIG. 6b.

In this manner, the scope corresponding unit adapted for the number of picture elements of the CCD is connected to the processor body, and the mask signal is switched depending upon the number of picture elements of the CCD of the electronic scope, whereby, in a case where a plurality of kinds of electronic scopes provided with CCDs different in the number of picture elements from each other are connected, it is possible that the appearing image plane on the monitor is so changed as to be brought to size adequate or optimum for the number of picture elements with minimum switching of the circuits.

The aforementioned various embodiments can be combined with each other partially or the like to form different embodiments, and such different embodiments belong to the present invention.

What is claimed is:

1. An image pickup system comprising:
    a first probe having an elongated first inserting section, and first image pickup means arranged adjacent to a forward end of said first inserting section, for forming an image of an object;
    a second probe having an elongated second inserting section, and second image pickup means arranged adjacent to a forward end of said second inserting section and different in signal form/function from said first image pickup means;
    a first adaptor unit detachably connected to said first probe through a cable for generating a drive signal adapted for signal form/function of said first image pickup means;
    a second adaptor unit detachably connected to said second probe through a cable for generating a drive signal adapted for signal form/function of said second image pickup means, said second adaptor unit being separate from said first adaptor unit;
    a body unit having a single connecting port to which one of either said first or second adaptor units is detachably connected, said body unit performing signal processing adapted for both said first and second image pickup means, to generate a standard image signal; and
    a monitor connected to said body unit, for displaying said image signal.

2. An image pickup system according to claim 1, wherein at least one of said first and second image pickup means comprises an electronic endoscope in which first and second image pickup elements having respective functions thereof performing photoelectric transfer are arranged respectively on focal surfaces of respective objective optical systems arranged adjacent to forward ends of the respective first and second inserting sections.

3. An image pickup system according to claim 2, wherein said electronic endoscope comprises an electronic endoscope of concurrent type in which a color filter array for color separation is arranged in front of image pickup surfaces of the respective first and second image pickup elements.

4. An image pickup system according to claim 2, wherein said electronic endoscope comprises an electronic endoscope of surface sequential image pickup type having no color filter array for color separation, in front of image pickup surfaces of the respective first and second image pickup elements.

5. An image pickup system according to claim 2, wherein aid electronic endoscope comprises a freeze switch for displaying a still picture.

6. An image pickup system according to claim 1, wherein at least one of said first and second probes comprises an endoscope of type in which a TV camera is mounted on the outside, comprising an optical endoscope including an image guide having one end surface thereof which is arranged on a focal surface of the objective optical system arranged adjacent to the forward ends of the respective first and second inserting sections, for transmitting an optical image to the other end surface, and a TV camera detachably connected to said optical endoscope and provided with first and second image pickup elements for photoelectrically transferring the optical image transmitted by said image guide.

7. An image pickup system according to claim 1, wherein at least one of said first and second image pickup means comprises an ultrasonic endoscope comprising first and second image pickup elements having such function as to perform photoelectric transfer on a focal surface of an objective optical system arranged adjacent to the forward ends of the respective first and second inserting sections, and an ultrasonic vibrator arranged adjacent to the forward ends of the respective first and second inserting sections, for performing image picking-up of an ultrasonic image.

8. An image pickup system according to claim 1, wherein at least one of said first and second image pickup means includes an ultrasonic vibrator arranged adjacent to the forward ends of the respective first and second inserting sections, for performing image picking-up of an ultrasonic image.

9. An image pickup system according to claim 1, wherein said first and second adaptor units include first and second drive-signal generating circuits for forming respectively said first and second image pickup means, for applying drive signals for outputting image pickup signals different in signal form from each other, image-picked-up from first and second image pickup elements having respective functions for conversion to electric signals.

10. An image pickup system according to claim 9, wherein one of the image pickup signals outputted respectively from said first and second image pickup elements consists of a color signal of time series, while the other consists of a coincidence color signal.

11. An image pickup system according to claim 1, wherein said first and second drive-signal generating circuits generate drive signals corresponding respectively to the numbers of picture elements different from each other.

12. Am image pickup system according to claim 1, wherein said first and second adaptor units include signal generating means for generating discrimination signals which distinguish said first and second adaptor units.

13. An image pickup system according to claim 1, wherein said signal generating means comprises either an electrical or mechanical structure.

14. An image pickup system according to claim 1, wherein said body unit comprises discrimination means for discriminating said first or second adaptor unit which is connected to said body unit.

15. An image pickup system according to claim 14, wherein said body unit changes signal processing in said body unit with respect to said first or second image pickup means, on the basis of an output from said discrimination means.

16. An image pickup system according to claim 1, wherein said first and second probes include functions for generating discrimination signals for distinguishing said first and second probes from each other.

17. An image pickup system according to claim 16, wherein said first or second adaptor unit comprises discrimination means for discriminating said first and second probes from said discrimination signal.

18. An image pickup system according to claim 17, wherein an output from said discrimination means selects either a processing system of said first or second adaptor unit.

19. An image pickup system according to claim 1, wherein one of said first and second image pickup means comprises an image pickup element of concurrent type for performing color image pickup under white illumination, while the other image pickup means comprises an image pickup element of surface sequential type for performing color image pickup under surface-sequential illumination.

20. An image pickup system according to claim 1, wherein at least one of said first and second probes comprises an ultrasonic vibrator which sends and receives an ultrasonic wave.

21. An image pickup system according to claim 20, wherein at least one of said first and second adaptor units comprises an ultrasonic-vibrator drive circuit for driving said ultrasonic vibrator.

22. An image pickup system according to claim 20, wherein said body unit comprises an ultrasonic image-signal generating circuit performing signal processing for generating an image signal from a signal received by said ultrasonic vibrator.

23. An image pickup system according to claim 1, wherein said first image pickup means comprises an objective optical system arranged adjacent to a forward end of said first inserting section, a first image pickup element arranged in the vicinity of the focal surface of said objective optical system and having function performing photoelectric transfer, and an actuator for moving one of said objective optical system and said first image pickup element in an optical-axis direction.

24. An image pickup system according to claim 23, wherein said first adaptor unit comprises a driven circuit for driving said actuator.

25. An image pickup system according to claim 1, wherein said first image pickup means comprises an image pickup element for visible radiation for performing image pickup by light within a visible area, and an image pickup element for invisible radiation for performing image pickup by light out of the visible area.

26. An image pickup system according to claim 1, wherein said first or second image pickup means comprises an image pickup element for invisible radiation for performing image pickup by light out of a visible area.

27. An image pickup system according to claim 26, wherein said body unit comprises a signal processing circuit with respect to said image pickup element for invisible radiation.

28. An image pickup system according to claim 1, wherein at least one of said adaptor units comprises an ultrasonic vibrator drive circuit for driving said ultrasonic vibrator.

29. An image pickup system according to claim 1, including a peripheral unit which is connected to an image-signal output terminal of said body unit.

30. An image pickup system according to claim 1, wherein said body unit comprises isolation means for isolating a side of said first adaptor unit and a side of said second adaptor unit from each other.

31. An image pickup system according to claim 1, wherein said body unit comprises operating means for changing a characteristic of a signal processing system within said body unit.

32. A signal processing unit comprising:
first and second adaptor units detachably connectable to first and second probes, respectively, said first probe having a first image pickup means different in signal form/function from a second image pickup means contained in a second probe, for generating drive signals adapted respectively to a signal form/function of said first and second image pickup means, said first and second adaptor units being separate from each other; and a body unit having a single connecting port to which one of either said first or second adaptor units is detachably connected, said body unit performing signal processing adapted to said first and second image pickup means to generate a common image signal.

33. A signal processing unit according to claim 32, wherein said body unit includes isolation means for isolating respective sides of said first and second adaptor units from each other.

34. A signal processing unit according to claim 33, wherein at least one of said first and second adaptor units includes an ultrasonic vibrator drive circuit for driving said ultrasonic vibrator.

35. A signal processing unit according to claim 32, wherein said body unit includes an outline emphasizing circuit for emphasizing an outline of an image in said image signal.

36. A signal processing unit according to claim 32, wherein at least one of said first and second adaptor units includes a photoelectric-transfer image-pickup-element drive circuit for driving the photoelectric transfer image pickup element having function for performing photoelectric transfer.

37. A signal processing unit according to claim 32, wherein, in a case where said first or said second image pickup means includes a photoelectric transfer image pickup element having function for performing photoelectric transferring, said first or said second adaptor unit comprises a color separation circuit for electrically performing color separation.

38. A signal processing unit according to claim 37, wherein said first or said second adaptor unit comprises selective means for selectively outputting a signal passing through a color separation circuit and a signal which does not pass through the color separation circuit.

39. A signal processing unit according to claim 38, wherein said first or said second adaptor unit comprises a discrimination circuit for discriminating said first or said second probe connected respectively to said first or said second adaptor unit, and wherein said selective means is controlled by an output signal from said discrimination means.

40. A signal processing unit according to claim 37, wherein said first or said second image pickup means comprises an image pickup element of invisible light image pickup for performing image pickup by light within an area out of said visible radiation area and an image pickup element of concurrent type which is provided with a color filter array for color separation with respect to light within a visible radiation area on a photoelectric transfer surface of said photoelectric transfer image pickup element.

41. A signal processing unit according to claim 32, wherein, whenever said first or said second image pickup means includes a photoelectric transfer image pickup element having function of performing photoelectric transfer, said first or said second adaptor unit includes a light source unit.

42. A signal processing unit according to claim 32, including a light guide having function of transmitting illuminating light in a case where said first or said second image pickup means includes a photoelectric transfer image pickup element which has a function of performing photoelectric transfer.

43. A signal processing unit according to claim 42, wherein, whenever said first or said second image pickup means is image pickup means of surface sequential type in which a color filter array optically performing color separation is not arranged in front of an image pickup surface of said photoelectric transfer image pickup element, said first or said second adaptor unit includes a color filter for converting illuminating light transmitted by a light guide to surface-sequential illuminating light of time series.

44. A signal processing unit according to claim 32, wherein said first or said second adaptor unit comprises isolation means for isolating the circuit within said body unit and the circuit within said first or said second adaptor unit from each other.

45. A signal processing unit according to claim 32, including a third adaptor unit having a different function from said first and second adaptor units.

46. A signal processing unit according to claim 45, wherein said third adaptor unit includes functions of both said first and second adaptor units.

47. A signal processing unit according to claim 45, wherein said third adaptor unit comprises discrimination means for discriminating said first and second image pickup means from each other, which are connected to said third adaptor unit, and wherein a function of said third adaptor unit is so switched by the output signal from said discrimination means as to be adapted for said first and second image pickup means.

48. A signal processing unit comprising:
first and second adaptor units separate from each other and to which first and second probes having first and second image pickup means, respectively, which are different in signal form/function from each other, are detachably connectable, for respectively generating drive signals adapted for signal form/function of said first and second image pickup means; and a body unit to which said first and second adaptor units is connected, said body unit performing signal processing adapted for said first and second image pickup means, to generate a common image signal, wherein said first or said second adaptor unit is connected to said body unit through a light source unit for supplying illuminating light to said first or said second probe which is connected to said first or second adaptor unit.

49. A signal processing unit according to claim 48, wherein said first or said second adaptor unit is connected to said body unit through an electric cable.

50. A signal processing unit according to claim 48, wherein said first or said second probe includes a connector which is connected to a connector receptor for signal of said first or said second adaptor unit and a connector receptor for light source of said light source unit for supplying the illuminating light to said first or said second probe.

51. A signal processing unit to which a plurality of probes driven by drive signals differing from each other in signal form are detachably connected, to drive the output signal to said probes, said signal processing unit comprising:
a first drive-signal generating unit provided on a body, for generating an intermediate drive signal for driving said probes; and a second drive-signal generating unit provided on an adaptor which is detachable with respect to said body, for outputting a final drive signal for driving said probes, on the basis of said intermediate drive signal generated by said first drive-signal generating unit.

52. A signal processing unit according to claim 51, wherein said probes are an electronic endoscope in which an image pickup element having a function of performing photoelectric transfer is arranged on a focal surface of an objective optical system which is arranged adjacent to the forward end of said probe.

53. A signal processing unit according to claim 51, wherein said probes consist of an ultrasonic endoscope which includes an image pickup element having function of performing photoelectric transfer and an ultrasonic vibrator arranged adjacent to the forward end of said probe for performing image pickup of an ultrasonic image, on a focal surface of an objective optical system which is arranged adjacent to the forward end of said probe.

54. A signal processing unit according to claim 52, wherein said electronic endoscope consists of an electronic endoscope of surface sequential image pickup system having no color filter array for color separation in front of an image pickup surface of said image pickup element.

55. A signal processing unit according to claim 51, wherein said electronic endoscope consists of an electronic endoscope of concurrent type having a color filter array for color separation in front of an image pickup surface of said image pickup element.

56. A signal processing unit according to claim 51, wherein said probes include an image pickup element for invisible light for performing image pickup by light out of a visible area.

57. A signal processing unit according to claim 51, wherein said electronic endoscope includes an autofocus function.

58. A signal processing unit according to claim 51, wherein said first drive-signal generating unit comprises at least one of isolation means, synchronous-signal generating means, a power-source circuit, an A/D converting circuit, a D/A conversion circuit, a memory circuit, a y correction circuit, an AGC circuit, an NTSC/PAL encoder circuit, an outline emphasizing circuit, a video buffer circuit, a color matrix circuit and a CPU circuit.

59. A signal processing unit according to claim 51, wherein said first drive-signal generating unit comprises said second drive-signal generating unit or judging means for judging kind or type of said probes.

60. A signal processing unit according to claim 51, wherein said second drive-signal generating unit comprises at least one of an image pickup element drive circuit, an CDS circuit for extracting a signal component, and an isolation circuit for performing isolation.

61. A signal processing unit according to claim 51, wherein said second drive-signal generating unit comprises an actuator drive circuit for driving an autofocus actuator.

62. A signal processing unit according to claim 51, wherein said second drive-signal generating unit comprises at least one of non-volatile memory means, a preamplifier, and a color separation circuit.

63. A signal processing unit according to claim 51, wherein said second drive-signal generating unit comprises a vibrator drive circuit for driving an ultrasonic vibrator.

64. A signal processing unit according to claim 51, wherein said second drive-signal generating unit comprises a color filter for surface sequential image pickup.

65. A signal processing unit according to claim 51, wherein said second drive-signal generating unit comprises light source means.

66. A signal processing unit according to claim 51, wherein said second drive-signal generating unit comprises a light guide.

67. A signal processing unit in which one of a plurality of image pickup units for outputting signals differing from each other in signal form is detachably connected, for outputting a drive signal to said image pickup units, said signal processing unit comprising:
a synchronous signal generating section mounted on a body for generating a synchronous signal; and
image pickup unit drive means arranged on a single adaptor detachable to said body, for outputting a drive signal for driving said image pickup unit, on the basis of said synchronous signal.

68. A signal processing unit to which a plurality of probes outputting signals different in signal form from each other are detachably connected, for processing signals outputted from said probes, said signal processing unit comprising:
a first signal processing unit provided on an adaptor which is detachable from a body, for subjecting intermediate processing to said signals outputted from said probes; and
a second signal processing unit provided on said body, for subjecting final processing to signals to which intermediate processing is subjected, by said first signal processing unit.

69. A signal processing apparatus to which a plurality of image pickup devices for outputting signals different in signal form from each other are detachably connected, for processing signals outputted from said image pickup devices, said signal processing unit comprising:
extracting means provided on an adaptor which is detachable on a body, for extracting an image signal component from an image pickup signal outputted from said image pickup devices; and
image-signal processing means provided on said body, for subjecting processing with respect to the image signal component extracted by said extracting means, to generate a signal capable of being displayed on a monitor.

70. A signal processing apparatus comprising:
first and second adaptor units to which first and second probes different in signal form from each other are connectable, and having drive functions correspondingly respectively to said first and second probes; and
a body unit having a single connecting port to which one of either said first or second adaptor units is detachably connected, for performing signal processing with respect to said first and second probes.

71. A signal processing apparatus according to claim 70, wherein at least one of said first and second adaptor units includes a plurality of signal forms.

* * * * *